(12) United States Patent
Short et al.

(10) Patent No.: US 9,464,284 B2
(45) Date of Patent: *Oct. 11, 2016

(54) MIRAC PROTEINS

(75) Inventors: Jay M. Short, Del Mar, CA (US); Hwai Wen Chang, San Marcos, CA (US); Gerhard Frey, San Diego, CA (US)

(73) Assignee: Bioatla, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/255,676

(22) PCT Filed: Mar. 9, 2010

(86) PCT No.: PCT/US2010/026611
§ 371 (c)(1),
(2), (4) Date: Mar. 9, 2012

(87) PCT Pub. No.: WO2010/104821
PCT Pub. Date: Sep. 16, 2010

(65) Prior Publication Data
US 2012/0164127 A1    Jun. 28, 2012

Related U.S. Application Data

(60) Provisional application No. 61/209,489, filed on Mar. 9, 2009.

(51) Int. Cl.

| | |
|---|---|
| *C12P 21/06* | (2006.01) |
| *C12N 9/00* | (2006.01) |
| *C12N 15/10* | (2006.01) |
| *C07K 14/315* | (2006.01) |
| *C12N 9/72* | (2006.01) |
| *G01N 33/68* | (2006.01) |
| *C07K 7/06* | (2006.01) |
| *C07K 14/47* | (2006.01) |
| *C07K 14/575* | (2006.01) |
| *C12N 9/16* | (2006.01) |
| *C12N 9/50* | (2006.01) |
| *G01N 33/543* | (2006.01) |
| *G01N 33/573* | (2006.01) |
| *A61K 38/00* | (2006.01) |

(52) U.S. Cl.
CPC .............. *C12N 15/102* (2013.01); *C07K 7/06* (2013.01); *C07K 14/3153* (2013.01); *C07K 14/47* (2013.01); *C07K 14/575* (2013.01); *C07K 14/57545* (2013.01); *C07K 14/57563* (2013.01); *C12N 9/16* (2013.01); *C12N 9/50* (2013.01); *C12N 9/6459* (2013.01); *C12N 9/6462* (2013.01); *C12N 15/1058* (2013.01); *C12Y 304/21069* (2013.01); *C12Y 304/21073* (2013.01); *G01N 33/54306* (2013.01); *G01N 33/573* (2013.01); *G01N 33/6845* (2013.01); *A61K 38/00* (2013.01); *C12Y 302/01035* (2013.01); *C12Y 304/21007* (2013.01); *C12Y 304/23015* (2013.01); *C12Y 304/24029* (2013.01)

(58) Field of Classification Search
CPC ... C12N 15/1058; C12N 5/102; A61K 38/00
See application file for complete search history.

(56) References Cited

U.S. PATENT DOCUMENTS

| | | |
|---|---|---|
| 6,759,046 B1 | 7/2004 | Gaudernack et al. |
| 8,709,755 B2 | 4/2014 | Short et al. |
| 2003/0224444 A1* | 12/2003 | Sabbadini et al. ............. 435/7.1 |
| 2004/0091968 A1 | 5/2004 | Short et al. |
| 2005/0100985 A1 | 5/2005 | Short |
| 2005/0163769 A1 | 7/2005 | Ramakrishnan et al. |
| 2005/0260711 A1 | 11/2005 | Datta et al. |
| 2007/0009930 A1 | 1/2007 | Patten et al. |
| 2008/0131500 A1 | 6/2008 | Chang |
| 2009/0130718 A1 | 5/2009 | Short |
| 2009/0181048 A1 | 7/2009 | Kamei et al. |
| 2011/0030106 A1 | 2/2011 | Laga et al. |
| 2011/0111406 A1 | 5/2011 | Igawa et al. |
| 2012/0020987 A1 | 1/2012 | Hyde et al. |
| 2013/0336963 A1 | 12/2013 | Igawa et al. |

FOREIGN PATENT DOCUMENTS

| | | |
|---|---|---|
| EP | 2275443 A1 | 1/2011 |
| JP | 2002500040 A | 1/2002 |
| JP | 2002530436 A | 9/2002 |
| JP | 2003518359 A | 6/2003 |
| JP | 2004500019 A | 1/2004 |
| JP | 2008410466 A | 4/2008 |
| JP | 2008510466 A | 4/2008 |
| NO | WO9120918 A1 | 6/1997 |
| WO | WO9514710 A1 | 6/1995 |
| WO | WO9935243 A2 | 7/1999 |
| WO | WO9942578 A2 | 8/1999 |
| WO | WO9958552 A2 | 11/1999 |
| WO | WO0031238 A2 | 6/2000 |
| WO | WO0058517 A1 | 10/2000 |
| WO | WO03105757 A2 | 12/2003 |
| WO | WO 2006031370 A2 | 3/2006 |
| WO | WO2009068313 A2 | 6/2009 |
| WO | WO2009125825 A1 | 10/2009 |

OTHER PUBLICATIONS

Palackal, N., et al., "An Evolutionary Route to Xylanase Process Fitness." Protein Sci. 2004; vol. 13, pp. 494-503.

(Continued)

*Primary Examiner* — Reza Ghafoorian
(74) *Attorney, Agent, or Firm* — Mendelsohn Dunleavy, P.C.

(57) ABSTRACT

This disclosure relates to a method of generating conditionally active biologic proteins from wild type proteins, in particular therapeutic proteins, which are reversibly or irreversibly inactivated at the wild type normal physiological conditions. For example, evolved proteins are virtually inactive at body temperature, but are active at lower temperatures.

31 Claims, No Drawings

(56) References Cited

OTHER PUBLICATIONS

Solbak, A., et al., "Discovery of Pectin-Degrading Enzymes and Directed Evolution of a Novel Pectate Lyase for Processing Cotton Fabric", Journal of Biological Chemistry, vol. 280, No. 10, Mar. 11, 2005; pp. 9431-9438.
Decision of Rejection; Mailed Feb. 8, 2014 for corresponding CN Application No. 201080011465.7 with an English language abstract.
European Search Report; Mailed Mar. 4, 2014 for corresponding EP Application No. 10 751 262.6.
Chinese Office Action; Mailed Jan. 30, 2013 for related CN Application No. CN 201080011465.7.
Chinese Office Action; Mailed Sep. 2, 2013 for related CN Application No. CN 201080011465.7.
European Search Report; Mailed Sep. 25, 2012 for related EP Application No. 10751262.6.
Mexican Office Action; Mailed Apr. 15, 2013 for related MX Application No. MX/A/2011/009422.
Ghetie, V., et al., "Increasing the serum persistence of an IgG fragment by random mutagenesis," Nature Biotechnology, vol. 15, Jul. 1997, pp. 637-640.
Shields, R., et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, vol. 276, No. 9, Mar. 2, 2001, pp. 6591-6604.
Notice of Reasons for Refusal; Mailed Jul. 11, 2014 for the related JP Application No. 2011-554111.
Kondo, H., "Research on Rendering Lipase to be Highly Functional based on Atomic Resolution Three-Dimensional Structural Analysis," National Institute of Advanced Industrial Science and Technology Annual Report, 2002, vol. H14 (2002) FY, p. 444.
Chilean Office Action; Received May 23, 2014 for the corresponding CL Application No. 2222-2011 along with brief description of office action content.
Holt, J., et al., "Domain Antibodies: Proteins for Therapy," Trends in Biotechnology, Jan. 11, 2003, vol. 21, No. 11, pp. 484-490.
Wark, K., et al., "Latest Technologies for the Enhancement of Antibody Affinity," Advance Drug Delivery Reviews, Jul. 8, 2006, vol. 58, No. 5-6, pp. 657-670.
Rothe, A., et al., "In Vitro Display Technologies Reveal Novel Biopharmaceutics," Faseb Journal, Jan. 8, 2006, vol. 20, No. 10, pp. 1599-1610.
Worn, A., et al., "Stability Engineering of Antibody Single-Chain Fv Fragments," Journal of Molecular Biology, Feb. 2, 2001, vol. 305, No. 5, pp. 989-1010.
Jermutus, L., et al., "Tailoring In Vitro Evolution for Protein Affinity or Stability," PNAS. Feb. 1, 2001, vol. 96, No. 1, pp. 75-80.
File History for U.S. Appl. No. 13/523,509 as retrieved on Sep. 24, 2014.
File History for U.S. Appl. No. 14/196,950 as retrieved on Sep. 24, 2014.
File History for U.S. Appl. No. 14/464,059 as retrieved on Sep. 24, 2014.
File History for U.S. Appl. No. 14/483,980 as retrieved on Sep. 24, 2014.
Reexamination Notice; Mailed Mar. 31, 2015 for the corresponding CN Application No. 201080011465.7 along with an English abstract.
Non-Final Office Action; Mailed Nov. 19, 2014 for corresponding U.S. Appl. No. 14/464,059.
Non-Final Office Action; Mailed Nov. 20, 2014 for corresponding U.S. Appl. No. 14/196,950.
Shultz, P., et al., "A General Method for Site-Specific Incorporation of Unnatural Amino Acids into Proteins," Science, vol. 244, No. 14, Apr. 1989, pp. 182-188.
Boder, et al., "Yeast Surface Display for Directed Evolution of Protein Expression, Affinity, and Stability," Methods in Enzymology, 2000, vol. 328, pp. 430-444.
European Search Report; Mailed Dec. 18, 2014 for the corresponding EP Application No. 10 751 262.6.
Qin, Y., et al., "Engineering endoglucanase II from Trichoderma reesei to improve the catalytic efficiency at a higher pH optimum," Journal of Biothechnology, Elsevier Science Publishers, Amsterdam, NL, vol. 135, No. 2, Jun. 1, 2008, pp. 190-195.
Fang, T. Y., et al., "Protein engineering of Aspergillus awamori glucoamylase to increase its pH optimum," Protein Engineering Design and Selection, vol. 11, No. 5, May 1, 1998, pp. 383-388.
Giver, L., et al., "Directed evolution of a thermostable esterase," Proceedings of the National Academy of Sciences, U.S., vol. 95, No. 22, Oct. 27, 1998, pp. 12809-12813.
Lehmann, M., et al., "The consensus concept for thermostability engineering of proteins: Further proof of concept," Protein Engineering, Oxford University Press, Surrey, GB, vol. 15, No. 5, May 1, 2002, pp. 403-411.
Turunen, O., et al., "Engineering of multiple arginines into the Ser/Thr surface of Trichoderma reesei endo-1, 4[beta]xylanase II increases the thermotolerance and shifts the pH optimun towards alkaline pH," Protein Engineering, vol. 15, No. 2, Feb. 1, 2002, pp. 141-145.
Venturi, M., et al., "The Monoclonal Antibody 1F6 Identities a pH-dependent Conformational Change in the Hydrophilic Nh^ 2 Therminus of NhaA Na +/H+ Antiporter of *Escherichia coli*," The Journal of Biological Chemistry, vol. 273, Issue of Feb. 18 2000, pp. 4734-4742.
Koumenis, C., et al., "Hypoxia and the Unfolded Protein Response," Methods in Enzymology, Chapter 14, 2000, vol. 435, pp. 275-293.
Final Decision of Rejection; Mailed Mar. 3, 2015 for corresponding JP Application No. JP2011-554111.
European Office Action; Mailed Jan. 4, 2016 for EP Application No. 10751262.6.
Ito, Wataru, et al. "The His-probe method: effects of histidine residues introduced into the complementarity-determining regions of antibodies on antigen-antibody interactions at different pH values." FEBS letters 309.1 (1992): 85-88.
Japanese Pre-Trial Patentability Report; Mailed Aug. 24, 2015 for corresponding JP Application No. JP2015-012789.
Final Office Action; Mailed Jun. 10, 2015 for corresponding U.S. Appl. No. 14/196,950.
Final Office Action; Mailed Jun. 11, 2015 for corresponding U.S. Appl. No. 14/464,059.
Final Office Action; Mailed Jul. 29, 2015 for corresponding U.S. Appl. No. 14/483,980.
Tawfik, Dan S., et al. "pH on-off switching of antibody-hapten binding by site-specific chemical modification of tyrosine." Protein engineering 7.3 (1994): 431-434.
Murtaugh, Megan L., et al. "A combinatorial histidine scanning library approach to engineer highly pH-dependent protein switches." Protein Science 20.9 (2011): 1619-1631.
Igawa, Tomoyuki, et al. "Antibody recycling by engineered pH-dependent antigen binding improves the duration of antigen neutralization." Nature biotechnology 28.11 (2010): 1203-1207.
Engin, K., et al. "Extracellular pH distribution in human tumours." International Journal of Hyperthermia 11.2 (1995): 211-216.
"pH". (2015). In Wikipedia, The Free Encyclopedia. Retrieved 18:12, Oct. 23, 2015, from https://en.wikipedia.org/w/index.php?title=PH&.
Third Part Observation for Application No. EP0100751262: mailed Sep. 25, 2015.
van Pouderoyen, Gertie, et al. "The crystal structure of Bacillus subtili lipase: a minimal α/β hydrolase fold enzyme." Journal of molecular biology 309.1 (2001): 215-226.
Non-Final Office Action; Mailed Mar. 23, 2016 for US. Appl. No. 14/464,059.
Non-Final Office Action; Mailed Mar. 23, 2016 for US. Appl. No. 14/196,950.
Meijer, Per-Johan, et al. "Directed evolution of a type I antifreeze protein expressed in *Escherichia coli* with sodium chloride as selective pressure and its effect on antifreeze tolerance." Protein engineering 9.11 (1996): 1051-1054.

(56) References Cited

OTHER PUBLICATIONS

Japanese Notification of Reasons of Refusal; Mailed Jun. 7, 2016 for JP Application No. JP2015-134811.
KR Notification of Reason of Refusal; Mailed Jun. 13, 2016 for KR Application No. KR10-20117022908.

Non-Final Office Action; Mailed Jun. 15, 2016 for U.S. Appl. No. 14/483,980.
"Advances in Biochemical Engineering Biotechnology: Metabolic Engineering," vol. 73, Scheper, T. and Nielsen, J. editors, 2002, 193 pages.

* cited by examiner

MIRAC PROTEINS

RELATED APPLICATION INFORMATION

This application is being filed on 9 Mar. 2010, as a PCT International Patent application in the name of BioAtla, LLC, a U.S. limited liability corporation, applicant for the designation of all countries except the US, and Jay M. Short, Hwai Wen Chang, both citizens of the U.S., and Gerhard Frey, a citizen of Germany, applicants for the designation of the US only, and claims priority to U.S. Provisional Patent Application Ser. No. 61/209,489 filed Mar. 9, 2009, the entire contents of which are incorporated herein by this reference.

FIELD OF THE DISCLOSURE

This disclosure relates to the field of protein evolution and activity. Specifically, this disclosure relates to a method of generating conditionally active biologic proteins from wild type proteins, in particular therapeutic proteins, and which are reversibly or irreversibly inactivated at the wild type normal physiological conditions. For example, evolved proteins are virtually inactive at body temperature, but are active at lower temperatures.

BACKGROUND OF THE DISCLOSURE

There is a considerable body of literature describing the potential for evolving proteins for a variety of characteristics, especially enzymes for example, to be stabilized for operation at different conditions. For example, enzymes have been evolved to be stabilized at higher temperatures, with varying activity. In situations where there is an activity improvement at the high temperature, a substantial portion of the improvement can be attributed to the higher kinetic activity commonly described by the Q10 rule where it is estimated that in the case of an enzyme the turnover doubles for every increase of 10 degrees Celsius. In addition, there exist examples of natural mutations that destabilize proteins at their normal operating conditions, such as wild-type temperature activity of the molecule. For temperature mutants, these mutants can be active at the lower temperature, but typically are active at a reduced level compared to the wild type molecules (also typically described by a reduction in activity guided by the Q10 or similar rules).

It is desirable to generate useful molecules that are conditionally activated, for example virtually inactive at wild-type conditions but are active at other than wild-type conditions at a level that is equal or better than at wild-type conditions, or that are activated or inactivated in certain microenvironments, or that are activated or inactivated over time. Besides temperature, other conditions for which the proteins can be evolved or optimized include pH, osmotic pressure, osmolality, oxidation and electrolyte concentration. Other desirable properties that can be optimized during evolution include chemical resistance, and proteolytic resistance.

Many strategies for evolving or engineering molecules have been published. However, engineering or evolving a protein to be inactive or virtually inactive (less than 10% activity and especially 1% activity) at its wild type operating condition, while maintaining activity equivalent or better than its wild type condition at new conditions, requires that the destabilizing mutation(s) co-exist with activity increasing mutations that do not counter the destabilizing effect. It is expected that destabilization would reduce the protein's activity greater than the effects predicted by standard rules such as Q10, therefore the ability to evolve proteins that work efficiently at lower temperature, for example, while being inactivated under their normal operating condition, creates an unexpected new class of proteins we refer to as Mirac Proteins.

Throughout this application, various publications are referenced by author and date. The disclosures of these publications in their entireties are hereby incorporated by reference into this application in order to more fully describe the state of the art as known to those skilled therein as of the date of the disclosure described and claimed herein.

SUMMARY OF THE DISCLOSURE

The disclosure provides a method of preparing a conditionally active biologic protein, the method comprising: selecting a wild-type biologic protein; evolving the DNA which encodes the wild-type biologic protein using one or more evolutionary techniques to create a mutant DNA; expressing the mutant DNA to obtain a mutant protein; subjecting the mutant protein and the wild-type protein to an assay under a normal physiological condition and the assay under an aberrant condition; and selecting the conditionally active biologic protein from those mutant proteins which exhibit both (a) a decrease in activity in the assay at the normal physiological condition compared to the wild-type protein, and (b) an increase in activity in the assay under the aberrant condition compared to the wild-type protein. In various aspects, the normal physiological condition is selected from one or more of temperature, pH, osmotic pressure, osmolality, oxidation and electrolyte concentration. In a particular aspect, the normal physiological condition is temperature; wherein the conditionally active biologic protein is virtually inactive at the normal physiological temperature, but is active at an aberrant temperature less than the normal physiological temperature. In other aspects, the conditionally active biologic protein is reversibly or irreversibly inactivated at the wild type normal physiological conditions. In one specific aspect, the protein is reversibly inactivated at the wild type normal physiological conditions. Alternatively, conditionally active biologic proteins are selected from those proteins which exhibit changes in activity, reversibly or irreversibly, in two or more different physiological conditions.

In one embodiment, the wild-type biologic protein is an enzyme. In certain aspects, the wild-type biologic protein is selected from the group consisting of tissue plasminogen activator, streptokinase, urokinase, renin, and hyaluronidase.

In another embodiment, the wild-type biologic protein is selected from calcitonin gene-related peptide (CGRP), substance P (SP), neuropeptide Y (NPY), vasoactive intestinal peptide(VIP), vasopressin, and angiostatin.

In another embodiment, the biologic protein is an antibody.

In another embodiment, the disclosure provides a method of preparing a conditionally active biological response modifier, the method comprising: selecting an inflammatory response mediator; identifying a wild-type antibody to the mediator; evolving the wild-type antibody; screening differentially for mutants that exhibit decreased binding to the mediator relative to the wild-type antibody at a first condition, and exhibit increased binding affinity to the mediator at a second condition to identify up-mutants; and recombining the heavy chains and the light chains of the up-mutants to create recombined up-mutants; and screening the recombined up-mutants for mutants that exhibit decreased binding to the mediator relative to the wild-type antibody at the first condition, and show increased binding affinity to the mediator at the second condition to identify the conditionally active biological response modifier. In one aspect, the inflammatory response mediator is selected from IL-6, IL-6 receptor, TNF-alpha, IL-23 and IL-12. In another aspect, the first and second conditions are selected from conditions of pH, osmotic pressure, osmolality, oxidation and electrolyte concentration.

In another embodiment, the disclosure provides a pharmaceutical composition comprising a conditionally active biologic protein, and a phaunaceutically acceptable carrier.

DETAILED DESCRIPTION

In order to facilitate understanding of the examples provided herein, certain frequently occurring methods and/or terms will be described.

As used herein in connection with a measured quantity, the term "about" refers to the normal variation in that measured quantity that would be expected by the skilled artisan making the measurement and exercising a level of care commensurate with the objective of the measurement and the precision of the measuring equipment used. Unless otherwise indicated, "about" refers to a variation of +/−10% of the value provided.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made from biological materials such as bacteria, plants, fungi, or animal (particular mammalian) cells or tissues. Agents are evaluated for potential enzyme activity by inclusion in screening assays described herein below. Agents are evaluated for potential activity as conditionally active biologic therapeutic enzymes by inclusion in screening assays described herein below.

An "ambiguous base requirement" in a restriction site refers to a nucleotide base requirement that is not specified to the fullest extent, i.e. that is not a specific base (such as, in a non-limiting exemplification, a specific base selected from A, C, G, and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

The term "amino acid" as used herein refers to any organic compound that contains an amino group ($—NH_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" means that the number of copies of a polynucleotide is increased.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assembling a reassortment of partial molecular sequences. In a non-limiting aspect, a chimeric polynucleotide molecule may be prepared by synthesizing the chimeric polynucleotide using plurality of molecular templates, such that the resultant, chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, 1981, "Comparison of biosequences", Adv Appl Math, 2:482-489; Smith and Waterman, 1981, "Overlapping genes and information theory", J Theor Biol,91:379-380; Smith and Waterman, J Mol Biol, "Identification of common molecular subsequences",1981, 147:195-197; Smith et al., 1981, ""Comparative biosequence metrics", J Mol Evol, 18:38-46), by the homology alignment algorithm of Needleman (Needleman and Wunsch, 1970, "A general method applicable to the search for similarities in the amino acid sequence of two proteins" J Mol Biol, 48(3):443-453), by the search of similarity method of Pearson (Pearson and Lipman, 1988, "Improved tools for biological sequence comparison", Proc Nat Acad Sci USA, 85:2444-2448), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "conditionally active biologic protein" refers to a variant, or mutant, of a wild-type protein which is more or less active than the parent wild-type protein under one or more normal physiological conditions. This conditionally active protein also exhibits activity in selected regions of the body and/or exhibits increased or decreased activity under aberrant, or permissive, physiological conditions. Normal physiological conditions are those of temperature, pH, osmotic pressure, osmolality, oxidation and electrolyte concentration which would be considered within a normal range at the site of administration, or at the tissue or organ at the site of action, to a subject. An aberrant condition is that which deviates from the normally acceptable range for that condition. In one aspect, the conditionally active biologic protein is virtually inactive at wild-type conditions but is active at other than wild-type conditions at a level that is equal or better than at wild-type conditions. For example, in one aspect, an evolved conditionally active biologic protein is virtually inactive at body temperature, but is active at lower temperatures. In another aspect, the conditionally active biologic protein is reversibly or irreversibly inactivated at the wild type conditions. In a further aspect, the wild-type protein is a therapeutic protein. In another aspect, the conditionally active biologic protein is used as a drug, or therapeutic agent. In yet another aspect, the protein is more or less active in highly oxygenated blood, such as, for example, after passage through the lung or in the lower pH environments found in the kidney.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "degrading effective" amount refers to the amount of enzyme which is required to process at least 50% of the substrate, as compared to substrate not contacted with the enzyme.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a .beta.-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues, and the like, either segmentally or over the entire length of the individual selected library member sequence. Defined sequence kernels can refer to either amino acid sequences or polynucleotide sequences. Of illustration and not limitation, the sequences $(NNK)_{10}$ and $(NNM)_{10}$, wherein N represents A, T, G, or C; K represents G or T; and M represents A or C, are defined sequence kernels.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 microgram of plasmid or DNA fragment is used with about 2 units of enzyme in about 20 microliters of buffer solution. For the purpose of isolating DNA fragments for plasmid construction, typically 5 to 50 micrograms of DNA are digested with 20 to 250 units of enzyme in a larger volume. Appropriate buffers and substrate amounts for particular restriction enzymes are specified by the manufacturer. Incubation times of about 1 hour at 37 degrees C. are ordinarily used, but may vary in accordance with the supplier's instructions. After digestion the reaction is electrophoresed directly on a gel to isolate the desired fragment.

"Directional ligation" refers to a ligation in which a 5' end and a 3' end of a polynuclotide are different enough to specify a preferred ligation orientation. For example, an otherwise untreated and undigested PCR product that has two blunt ends will typically not have a preferred ligation orientation when ligated into a cloning vector digested to produce blunt ends in its multiple cloning site; thus, directional ligation will typically not be displayed under these circumstances. In contrast, directional ligation will typically be displayed when a digested PCR product having a 5' EcoR I-treated end and a 3' BamH I is ligated into a cloning vector that has a multiple cloning site digested with EcoR I and BamH I.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like. DNA shuffling can be random or non-random.

The term "drug" or "drug molecule" refers to a therapeutic agent including a substance having a beneficial effect on a human or animal body when it is administered to the human or animal body. Preferably, the therapeutic agent includes a substance that can treat, cure or relieve one or more symptoms, illnesses, or abnormal conditions in a human or animal body or enhance the wellness of a human or animal body.

An "effective amount" is an amount of a conditionally active biologic protein or fragment which is effective to treat or prevent a condition in a living organism to whom it is administered over some period of time, e.g., provides a therapeutic effect during a desired dosing interval.

As used herein, the term "electrolyte" is used to define a mineral in the blood or other body fluids that carries a charge. For example, in one aspect, the normal physiological condition and aberrant condition can be conditions of "electrolyte concentration". In one aspect, the electrolyte concentration to be tested is selected from one or more of ionized calcium, sodium, potassium, magnesium, chloride, bicarbonate, and phosphate concentration. For example, in one aspect, normal range of serum calcium is 8.5 to 10.2 mg/dL. In this aspect, aberrant serum calcium concentration may be selected from either above or below the normal range. In another example, in one aspect, normal range of serum chloride is 96-106 milliequivalents per liter (mEq/L). In this aspect, aberrant serum chloride concentration may be selected from either above or below the normal range. In another example, in one aspect, a normal range of serum magnesium is from 1.7-2.2 mg/dL. In this aspect, an aberrant serum magnesium concentration may be selected from either above or below the normal range. In another example, in one aspect, a normal range of serum phosphorus is from 2.4 to 4.1 mg/dL. In this aspect, aberrant serum phosphorus concentration may be selected from either above or below the normal range. In another example, in one aspect, a normal range of serum, or blood, sodium is from 135 to 145 mEq/L. In this aspect, aberrant serum, or blood, sodium concentration may be selected from either above or below the normal range. In another example, in one aspect, a normal range of serum, or blood, potassium is from 3.7 to 5.2 mEq/L. In this aspect, aberrant serum, or blood, potassium concentration may be selected from either above or below the normal range. In a further aspect, a normal range of serum bicarbonate is from 20 to 29 mEq/L. In this aspect, aberrant serum, or blood, bicarbonate concentration may be selected from either above or below the normal range. In a different aspect, bicarbonate levels can be used to indicate normal levels of acidity (pH), in the blood. The term "electrolyte concentration" may also be used to define the condition of a particular electrolyte in a tissue or body fluid other than blood or plasma. In this case, the normal physiological condition is considered to be the clinically normal range for that tissue or fluid. In this aspect, aberrant tissue or fluid electrolyte concentration may be selected from either above or below the normal range.

As used in this disclosure, the term "epitope" refers to an antigenic determinant on an antigen, such as an enzyme polypeptide, to which the paratope of an antibody, such as an enzyme-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

As used herein, an "enzyme" is a protein with specific catalytic properties. Factors such as, for example, substrate concentration, pH, temperature and presence or absence of inhibitors can affect the rate of catalysis. Typically, for a wild type enzyme, Q10 (the temperature coefficient) describes the increase in reaction rate with a 10 degree C. rise in temperature. For wild type enzymes, the Q10=2 to 3; in other words, the rate of reaction doubles or triples with every 10 degree increase in temperature. At high temperatures, proteins denature. At pH values slightly different from an enzymes optimum value, small changes occur in the charges of the enzyme and perhaps the substrate molecule. The change in ionization can affect the binding of the substrate molecule. At extreme pH levels, the enzyme will produce denaturation, where the active site is distorted, and the substrate molecule will no longer fit.

As used herein, the term "evolution", or "evolving", refers to using one or more methods of mutagenesis to generate a novel polynucleotide encoding a novel polypeptide, which novel polypeptide is itself an improved biological molecule &/or contributes to the generation of another improved biological molecule. In a particular non-limiting aspect, the present disclosure relates to evolution of conditionally active biologic proteins from a parent wild type protein. In one aspect, for example, evolution relates to a method of performing both non-stochastic polynucleotide chimerization and non-stochastic site-directed point mutagenesis disclosed in U.S. patent application publication 2009/0130718, which is incorporated herein by reference. More particularly, the present disclosure provides methods for evolution of conditionally active biologic enzymes which exhibit reduced activity at normal physiological conditions compared to a wild-type enzyme parent molecule, but enhanced activity under one or more aberrant conditions compared to the wild-type enzyme.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

A method is provided herein for producing from a template polypeptide a set of progeny polypeptides in which a "full range of single amino acid substitutions" is represented at each amino acid position. As used herein, "full range of single amino acid substitutions" is in reference to the 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (introns) between individual coding segments (exons).

"Genetic instability", as used herein, refers to the natural tendency of highly repetitive sequences to be lost through a process of reductive events generally involving sequence simplification through the loss of repeated sequences. Deletions tend to involve the loss of one copy of a repeat and everything between the repeats.

The term "heterologous" means that one single-stranded nucleic acid sequence is unable to hybridize to another single-stranded nucleic acid sequence or its complement. Thus areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The benefits of this disclosure extend to "industrial applications" (or industrial processes), which term is used to include applications in commercial industry proper (or simply industry) as well as non-commercial industrial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The term "isolated nucleic acid" is used to define a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Sambrook et al., (1982). Molecular Cloning: A Laboratory Manual. Cold Spring Harbour Laboratory, Cold Spring Harbor, NY., p. 146; Sambrook et al., Molecular Cloning: a laboratory manual, $2^{nd}$ Ed., Cold Spring Harbor Laboratory Press, 1989). Unless otherwise provided, ligation may be accomplished using known buffers and conditions with 10 units of T4 DNA ligase ("ligase") per 0.5 micrograms of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

As used herein "microenvironment" means any portion or region of a tissue or body that has constant or temporal, physical or chemical differences from other regions of the tissue or regions of the body.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting—examples of molecular properties to be evolved include protein activities at specified conditions, such as related to temperature; salinity; osmotic pressure; pH; oxidation, and concentration of glycerol, DMSO, detergent, &/or any other molecular species with which contact is made in a reaction environment. Additional particularly relevant—but by no means limiting—examples of molecular properties to be evolved include stabilities—e.g. the amount of a residual molecular property that is present after a specified exposure time to a specified environment, such as may be encountered during storage.

The term "mutations" means changes in the sequence of a wild-type nucleic acid sequence or changes in the sequence of a peptide. Such mutations may be point mutations such as transitions or transversions. The mutations may be deletions, insertions or duplications.

As used herein, the degenerate "N,N,G/T" nucleotide sequence represents 32 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (un-diseased) individual, such as would be typical for the species.

As used herein, "normal physiological conditions", or "wild type operating conditions", are those conditions of temperature, pH, osmotic pressure, osmolality, oxidation and electrolyte concentration which would be considered within a normal range at the site of administration, or the site of action, in a subject.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable to its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present disclosure provides a "nucleic acid construct" or alternatively a "nucleotide construct" or alternatively a "DNA construct". The term "construct" is used herein to describe a molecule, such as a polynucleotide (e.g., an enzyme polynucleotide) which may optionally be chemically bonded to one or more additional molecular moieties, such as a vector, or parts of a vector. In a specific—but by no means limiting—aspect, a nucleotide construct is exemplified by DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "parental polynucleotide set" is a set comprised of one or more distinct polynucleotide species. Usually this term is used in reference to a progeny polynucleotide set which is preferably obtained by mutagenization of the parental set, in which case the terms "parental", "starting" and "template" are used interchangeably.

The term "patient", or "subject", refers to an animal, for example a mammal, such as a human, who is the object of treatment. The subject, or patient, may be either male or female.

As used herein the term "physiological conditions" refers to temperature, pH, osmotic pressure, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45 degrees C. and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants. Normal physiological conditions refer to conditions of temperature, pH, osmotic pressure, osmolality, oxidation and electrolyte concentration in vivo in a patient or subject at the site of administration, or the site of action, which would be considered within the normal range in a patient.

Standard convention (5' to 3') is used herein to describe the sequence of double standed polynucleotides.

The term "population" as used herein means a collection of components such as polynucleotides, portions or polynucleotides or proteins. A "mixed population" means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modifications (e.g. two proteolytic cleavages, or a proteolytic cleavage and a deglycosylation) can be distinguished en route to the production of a mature molecule, the reference precursor molecule may be termed a "pre-pro-form" molecule.

As used herein, the term "pseudorandom" refers to a set of sequences that have limited variability, such that, for example, the degree of residue variability at another position, but any pseudorandom position is allowed some degree of residue variation, however circumscribed.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reasserted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins that contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoR I site) or an immediately adjacent cleavage site (e.g./CCWGG in the EcoR II site). In other cases, relevant restriction enzymes [e.g. the Eco57 I site or CTGAAG(16/14)] contain a low ambiguity sequence (e.g. the CTGAAG sequence in the Eco57 I site) with an external cleavage site (e.g. in the N.sub.16 portion of the Eco57 I site). When an enzyme (e.g. a restriction enzyme) is said to "cleave" a polynucleotide, it is understood to mean that the restriction enzyme catalyzes or facilitates a cleavage of a polynucleotide.

In a non-limiting aspect, a "selectable polynucleotide" is comprised of a 5' terminal region (or end region), an intermediate region (i.e. an internal or central region), and a 3'terminal region (or end region). As used in this aspect, a 5' terminal region is a region that is located towards a 5' polynucleotide terminus (or a 5' polynucleotide end); thus it is either partially or entirely in a 5' half of a polynucleotide. Likewise, a 3' terminal region is a region that is located towards a 3' polynucleotide terminus (or a 3' polynucleotide end); thus it is either partially or entirely in a 3' half of a polynucleotide. As used in this non-limiting exemplification, there may be sequence overlap between any two regions or even among all three regions.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25-50 nucleotides, wherein the percentage of sequence identity is calculated by comparing the reference sequence to the polynucleotide sequence which may include deletions or additions which total 20 percent or less of the reference sequence over the window of comparison.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

"Stringent hybridization conditions" means hybridization will occur only if there is at least 90% identity, preferably at least 95% identity and most preferably at least 97% identity between the sequences. See Sambrook et al., Molecular Cloning: a laboratory manual, $2^{nd}$ Ed., Cold Spring Harbor Laboratory Press, 1989, which is hereby incorporated by reference in its entirety.

Also included in the disclosure are polypeptides having sequences that are "substantially identical" to the sequence of an enzyme polypeptide. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site of the molecule, and provided that the polypeptide essentially retains its behavioural properties. For example, one or more amino acids can be deleted from an enzyme polypeptide, resulting in modification of the structure of the polypeptide, without significantly altering its biological activity. For example, amino- or carboxyl-terminal amino acids that are not required for enzyme biological activity can be removed. Such modifications can result in the development of smaller active enzyme polypeptides.

The present disclosure provides a "substantially pure enzyme". The term "substantially pure enzyme" is used herein to describe a molecule, such as a polypeptide (e.g., an enzyme polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "treating" includes: (1) preventing or delaying the appearance of clinical symptoms of the state, disorder or condition developing in an animal that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician.

As used herein, the term "variable segment" refers to a portion of a nascent peptide which comprises a random, pseudorandom, or defined kernal sequence. A "variable segment" refers to a portion of a nascent peptide which comprises a random pseudorandom, or defined kernal sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

The term "variant" refers to polynucleotides or polypeptides of the disclosure modified at one or more base pairs, codons, introns, exons, or amino acid residues (respectively) of a wild-type protein parent molecule. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, saturation mutagenesis and any combination thereof. Techniques for producing variant proteins having reduced activity compared to the wild-type protein at a normal physiological condition of e.g., one or more conditions of temperature, pH, osmotic pressure, osmolality, oxidation and electrolyte concentration; and enhanced activity at an aberrant condition, are disclosed herein. Variants may additionally be selected for the properties of enhanced chemical resistance, and proteolytic resistance, compared to the wild-type protein.

As used herein, the term "wild-type" means that the polynucleotide does not comprise any mutations. A "wild type protein", "wild-type protein", "wild-type biologic protein", or "wild type biologic protein", refers to a protein which can be isolated from nature that will be active at a level of activity found in nature and will comprise the amino acid sequence found in nature. The terms "parent molecule" and "target protein" also refer to the wild-type protein.

The term "working", as in "working sample", for example, is simply a sample with which one is working. Likewise, a "working molecule", for example is a molecule with which one is working.

The present disclosure is directed to methods of engineering or evolving proteins to generate new molecules that are reversibly or irreversibly inactivated at the wild type condition, but active at non-normal conditions at the same or equivalent level as the wild-type condition. These new proteins are referred to as "Mirac" proteins herein. Mirac proteins are particularly valuable for development of novel therapeutics that are active for short or limited periods of time within the host. This is particularly valuable where extended operation of the protein at the given dose would be harmful to the host, but where limited activity is required to perform the desired therapy. Examples of beneficial applications include topical or systemic treatments at high dose, as well as localized treatments in high concentration. Inactivation under the physiological condition can be determined by a combination of the dosing and the rate of inactivation of the protein. This condition based inactivation is especially important for enzyme therapeutics where catalytic activity cause substantial negative effects in a relatively short period of time.

The present disclosure is also directed to methods of engineering or evolving proteins to generate new molecules that are different from wild type molecules in that they are reversibly or irreversibly activated or inactivated over time, or activated or inactivated only when they are in certain microenvironments in the body, including in specific organs in the body (such as the bladder or kidney).

Target Wild-Type Proteins

Any therapeutic protein can serve as a target protein, or wild-type protein, for production of a conditionally active biologic protein. In one aspect, the target protein is a wild-type enzyme. Currently used therapeutic enzymes include urokinase and streptokinase, used in the treatment of blood clots; and hyaluronidase, used as an adjuvant to improve the absorption and dispersion of other drugs. In one aspect, the wild-type protein selected for generation of a conditionally active biologic protein can be a currently used therapeutic enzyme, in order to avoid or minimize deleterious side effects associated with the wild-type protein or enzyme. Alternatively, an enzyme not in current usage as a therapeutic can be selected for generation of a conditionally active biologic protein. Certain non-limiting examples will be discussed in further detail below.

Therapeutic proteins are those which can be used in medicine either alone or in conjunction with other therapies to treat various diseases or medical conditions. The conditionally active biologic proteins of the disclosure could be appropriate for use in one or more indications including the treatment of circulatory disorders, arthritis, multiple sclerosis, autoimmune disorders, cancer, dermatologic conditions and use in various diagnostic formats. Depending on the protein and indication, the conditionally active biologic enzyme protein could be administered in parenteral, topical or oral formulations as discussed below.

Circulatory Disorders—Thrombosis and Thrombolytic Therapy

A thrombus (blood clot) is defined as a solid mass derived from blood constituents that forms in the circulatory system. The thrombus is formed by a series of events involving blood coagulation factors, platelets, red blood cells, and interactions with the vessel wall. A platelet is an intravascular aggregation of platelets, fibrin and entrapped blood cells which can cause vascular obstruction. By obstructing or blocking blood flow, the thrombus deprives downstream tissue of oxygen supply. Fragments (emboli) of the thrombus may break away and obstruct smaller vessels. Arterial thrombus formation is precipitated by any of a variety of factors including an underlying stenosis-atherosclerosis, a low flow state-cardiac function, hypercoagubility as in cancer or a coagulation factor deficiency, or a foreign body such as a stent or catheter. A thrombus leading to arterial ischemia can result in limb or tissue injury, acute myocardial infarction (AMI), stroke, amputation, or bowel infarction. Major causes of morbidity and mortality are the formation of arterial thrombi (coronary arterial thrombi and cerebral arterial thrombi) and pulmonary thrombi. Venous thrombus formation can occur due to endothelial injury such as trauma, stasis due to e.g. immobility, or hypercoagulability, but atherosclerosos is not a factor. Treatment strategies include mechanical thrombectomy, pharmacomechanical thrombectomy and thrombolysis. Thrombotic therapy is used to minimize formation and aid in removal of thrombi.

Thrombotic therapy includes the use of antiplatelet agents which inhibit platelet activation, anticoagulant therapies, and/or thrombolytic therapy to degrade blood clots. Examples of antiplatelets include aspirin, dipyridamole, and ticlopidine. Examples of anticoagulants include heparin, warfarin, hirudin, and activated human protein C. Examples of thrombolytics include tissue plasminogen activator (tPA)/tPA variants, urokinase and streptokinase. The thrombolytics display a catalytic mode of action.

Thrombolytic therapy in acute myocardial infarction is well established. Use of thrombolytic agents has become standard emergency treatment. Although effective, these products achieve complete reperfusion in only about 50% of patients and side effects include risk of hemorrhage (in particular intracranial bleeding) as well as hypertension. The degradation of blood clots from a damaged or diseased vessel is termed "fibrinolysis" or the "fibrinolytic process". Fibrinolysis is a proteolytic process, by a plasminogen activator which activates the protein plasminogen, thereby forming plasmin. Plasmin proteolytically degrades the fibrin strands of the blood clot to dissolve the clot. Fibrin specific plasminogen activators include tissue plasminogen activators or variants. Non-specific plasminogen activators can include streptokinase and urokinase.

Certain commonly used thrombolytic therapies utilize one of several available tissue plasminogen activator (tPA) variants. For example, tPA based product variants which have been previously approved for use are Alteplase (rt-PA), Reteplase (r-PA) and Tenecteplase (TNK). Approved uses for tPA variants include, for example, acute myocardial infarction for the improvement of ventricular function following AMI, the reduction of incidence of congestive heart failure, and reduction of mortality associated with AMI, management of ischemic stroke in adults for improving neurological recovery and reducing incidence of disability, management of acute massive pulmonary embolism in adults for the lysis of acute pulmonary emboli, and for the lysis of pulmonary emboli accompanied by unstable hemodynamics.

Another commonly used thrombolytic therapy utilizes urokinase. Urokinase is a standard lytic agent used in the management of peripheral vascular disease.

Streptokinase is a protein secreted by several species of streptococci that can bind and activate human plasminogen. Complexes of streptokinase with human plasminogen can hydrolytically activate other unbound plasminogen by activating through bond cleavage to produce plasmin. The usual activation of plasminogen is through the proteolysis of the Arg561-Val562 bond. The amino group of Val562 then forms a salt-bridge with Asp740, which causes a conformational change to produce the active protease plasmin. Plasmin is produced in the blood to break down fibrin, the major constituent of blood clots.

Streptokinase is used as an effective clot-dissolving medication in some cases of myocardial infarction (heart attack), pulmonary embolism (lung blood clots), and deep venous thrombosis (leg blood clots). Streptokinase belongs to a group of medications called fibrinolytics. Streptokinase is given as soon as possible after the onset of a heart attack to dissolve clots in the arteries of the heart wall and reduce damage to the heart muscle. Streptokinase is a bacterial product, so the body has the ability to build up immunity against the protein. Therefore, it is recommended that this product should not be given again after four days from the first administration, as it may not be as effective and cause an allergic reaction. For this reason it is usually given only after a first heart attack, and further thrombotic events are typically treated with tissue plasminogen activator (TPA). Streptokinase is also sometimes used to prevent post-operative adhesions.

Side effects of streptokinase include bleeding (major and minor), hypotension, and respiratory depression as well as possible allergic reaction. In addition, anticoagulants, agents that alter platelet function (e.g. aspirin, other NSAIDs, dipyridamole) may increase risk of bleeding.

Administration of the thrombolytics is generally by infusion or by bolus intravenous dose; or by a mechanical infusion system. Adverse effects can include serious intracranial, gastrointestinal, retroperitoneal, or pericardial bleeding. If bleeding occurs the administration must be discontinued immediately.

In certain embodiments of the disclosure, tPA, streptokinase or urokinase is selected as the target, or wild-type protein.

In one embodiment, the methods of the disclosure are used to select for a conditionally active recombinant or synthetic streptokinase variant with high activity at aberrant temperature conditions below normal physiological conditions; and substantial deactivation or inactivation at normal physiological conditions (e.g. 37 degrees C.). In one aspect, the aberrant temperature condition is room temperature, e.g. 20-25 degrees C. In another aspect, the disclosure provides a method of treating a stroke or heart attack, the method comprising administering a high dose of the conditionally active streptokinase variant to stroke or heart attack victims in order to clear clots, yet allow for rapid inactivation of the streptokinase variant to avoid excessive bleeding.

Circulatory Disorders—Renin/Angiotensin

The renin-angiotensin system is a hormone system that regulates blood pressure and water (fluid) balance. The kidneys secrete renin when the blood volume is low. Renin is an enzyme which hydrolyzes angiotensinogen secreted from the liver into the peptide angiotensin I. Angiotensin I is further cleaved in the lungs by endothelial-bound angiotensin converting enzyme (ACE) into angiotensin II, the most vasoactive peptide. Angiotensin II causes the blood vessels to constrict, resulting in increased blood pressure. However, angiotensin II also stimulates the secretion of the hormone aldosterone from the adrenal cortex. Aldosterone causes the tubules of the kidneys to increase the resorption of sodium and water. This increases the volume of fluid in the body, which also increases blood pressure. An overactive renin-angiotensin system leads to vasoconstriction and retention of sodium and water. These effects lead to hypertension. There are many drugs which interrupt different steps in this system to lower blood pressure. These drugs are one of the main ways to control high blood pressure (hypertension), heart failure, kidney failure, and harmful effects of diabetes.

Hypovolemic shock is an emergency condition in which severe blood and/or fluid loss makes the heart unable to adequately perfuse the body's cells with oxygenated blood. Blood loss can be from trauma, injuries and internal bleeding. The amount of circulating blood may drop due to excessive fluid loss from burns, diarrhea, excessive perspiration or vomiting. Symptoms of hypovolemic shock include anxiety, cool clammy skin, confusion, rapid breathing, or unconsciousness. Examination shows signs of shock including low blood pressure, low body temperature, and rapid pulse, which may be weak or thready. Treatment includes intravenous fluids; blood or blood products; treatment for shock; and medication such as dopamine, dobutamine, epinephrine and norepinephrine to increase blood pressure and cardiac output.

In one embodiment, the disclosure provides a method of selecting for a conditionally active recombinant renin variant to be reversibly deactivated at normal physiological temperature, but reactivated at the aberrant lower temperatures in a patient with hypovolemic shock. The conditionally active protein can be used to treat hypovolemic shock to help increase the volume of fluid in the body, and increase blood pressure.

Circulatory Disorders—Reynaud's Phenomenon

Reynaud's phenomenon (RP) is a vasospastic disorder causing discoloration of the fingers, toes and occasionally other extremities. Emotional stress and cold are classic triggers of the phenomenon. When exposed to cold temperatures, the extremities lose heat. The blood supply to fingers and toes is normally slowed to preserve the body's core temperature. Blood flow is reduced by the narrowing of small arteries under the skin of the extremities. Stress causes similar reaction to cold in the body. In Reynaud's, the normal response is exaggerated. The condition can cause pain, discoloration, and sensations of cold and numbness. The phenomenon is the result of vasospasms that decrease the blood supply to the respective regions. In Reynaud's disease (Primary Raynaud's phenomenon), the disease is idiopathic. In Raynaud's syndrome (Secondary Reynaud's), the phenomenon is caused by some other instigating factor. Measurement of hand-temperature gradients is one tool to distinguish between the primary and secondary forms. The primary form can progress to the secondary form, and in extreme cases, the secondary form can progress to necrosis or gangrene of the fingertips.

Raynaud's phenomenon is an exaggeration of responses to cold or emotional stress. Primary RP is essentially mediated by microvascular vasospasm. Hyperactivation of the sympathetic system causes extreme vasoconstriction of the peripheral blood vessels, leading to hypoxia. Chronic, recurrent cases can result in atrophy of the skin, subcutaneous tissue, and muscle. It can also rarely result in ulceration and ischemic gangrene.

Traditional treatment options for Reynaud's phenomenon include prescription medication that dilates blood vessels and promotes circulation. These include calcium channel blockers, such as nifedipine or diltiazem; alpha blockers, which counteract the actions of norepinephrine, a hormone that constricts blood vessels, such as prazosin or doxazosin; and vasodilators, to relax blood vessels, such as nitroglycerin cream, or the angiotensin II inhibitor losartan, sildenafil, or prostaglandins. Fluoxetine, a selective serotonin reuptake inhibitor and other antidepressant medications may reduce the frequency and severity of episodes due to psychological stressors. These drugs may cause side effects such as headache, flushing and ankle edema. A drug may also lose effectiveness over time.

The regulation of cutaneous vasoconstriction and vasodilation involves altered sympathetic nerve activity and a number of neuronal regulators, including adrenergic and non-adrenergic, as well as REDOX signaling and other signaling such as the RhoA/ROCK pathway. Vasoconstriction of vascular smooth muscle cells (vSMC) in the skin is thought to be activated by norepinephrine mediated by alpha1 and alpha2 adrenoreceptors. Alpha2C-ARs translocate from the trans Golgi to the cell surface of the vSMC where they respond to stimulation and signaling of these responses involves the RhoA/Rhokinase (ROCK) signaling pathway. Cold stimulation in cutaneous arteries results in the immediate generation of reactive oxygen species (ROS) in the vSMC mitochondria. ROS are involved in the REDOX signaling through the RhoA/ROCK pathway. RhoA is a GTP-binding protein whose role is the regulation of actin-myosin dependent processes such as migration and cell contraction in vSMC. Non-adrenergic neuropeptides with known function in vasculature with possible involvement in RP include calcitonin gene-related peptide (CGRP), Substance P (SP), Neuropeptide Y (NPY), and vasoactive intestinal peptide(VIP). Fonseca et al., 2009, "Neuronal regulators and vascular dysfunction in Raynaud's phenomenon and systemic sclerosis", Curr. Vascul. Pharmacol. 7:34-39.

New therapies for RP include alpha-2c adrenergic receptor blockers, protein tyrosine kinase inhibitors, Rho-kinase inhibitors and calcitonin gene related peptide.

Calcitonin gene related peptide (CGRP) is a member of the calcitonin family of peptides and exists in two forms; alpha-CGRP and beta-CGRP. Alpha-CGRP is a 37-amino acid peptide formed from alternative splicing of the calcitonin/CGRP gene. CGRP is one of the most abundant peptides produced in peripheral and central neurons. It is a potent peptide vasodilator and can function in the transmission of pain. Migraine is a common neurological disorder that is associated with an increase in CGRP levels. CGRP dilates intracranial blood vessels and transmits vascular nociception. CGRP receptor antagonists have been tested as treatments for migraines. Arulmani et al., 2004, "Calcitonin gene-related peptide and it role in migraine pathophysiology", Eur. J. Pharmacol. 500(1-3): 315-330. At least three receptor subtypes have been identified and CGRP acts through G protein-coupled receptors whose presence and changes in function modulate the peptide's effect in various tissues. CGRP's signal transduction through the receptors is dependent on two accessory proteins: receptor activity modifying protein 1 (RAMP1) and receptor component protein (RCP). Ghatta 2004, Calcitonin gene-related peptide: understanding its role. Indian J. Pharmacol. 36(5): 277-283. One study of the effects of intravenous infusion of three vasodilators: endothelium-dependent vasodilator adenosine triphosphate (ATP), endothelium-independent vasodilator prostacyclin (epoprostenol; PGI2), and CGRP, to patients with Reynaud's phenomenon, and a similar number of age and sex matched controls, using laser Doppler flowmetry (LDF) showed CGRP induced flushing of the face and hands by a rise in skin blood flow in the Reynaud's patients, whereas in controls CGRP caused flushing only in the face. PGI2 caused similar rises in blood flow in hands and face of both groups. ATP did not cause any significant changes in blood flow in hands or face of the patients, but increased blood flow to the face of controls. Shawket et al., 1989, "Selective suprasensitivity to calcitonin-gene-related peptide in the hands in Reynaud's phenomenon". The Lancet, 334(8676):1354-1357. In one aspect, the wild-type protein target molecule is CGRP.

In one embodiment, the disclosure provides methods of selecting for conditionally active recombinant protein variants of proteins associated with Reynaud's syndrome to be reversibly deactivated at normal physiological temperature, but reactivated at the aberrant lower temperatures in digits. The conditionally active proteins can be used to treat Reynaud's phenomenon, to prevent or reduce loss of digit function due to low circulation.

Circulatory Disorders—Vasopressin

Arginine vasopressin (AVP, vasopressin, antidiuretic hormone (ADH)) is a peptide hormone found in most mammals that controls reabsorption of molecules in the tubules of the kidney by affecting tissue permeability. One of the most important roles of vasopressin is to regulate water retention in the body. In high concentrations it raises blood pressure by introducing moderate vasoconstriction. Vasopressin has three effects which result in increased urine osmolality (increased concentration) and decreased water excretion. First, vasopressin causes an increase in the permeability of water of the collecting duct cells in the kidney allowing water resorption and excretion of a smaller volume of concentrated urine (antidiuresis). This occurs through insertion of aquaporin-2 water channels into the apical membrane of the collecting duct cells. Secondly, vasopressin causes an increase in the permeability of the inner medullary portion of the collecting duct to urea, allowing increased reabsorption urea into the medullary interstitium. Thirdly, vasopressin causes stimulation of sodium and chloride reabsorption in the thick ascending limb of the loop of Henle by increasing the activity of the $Na^+$—$K^+$-$2Cl^-$-cotransporter. NaCl reabsorption drives the process of countercurrent multiplication, which furnishes the osmotic gradient for aquaporin mediated water reabsorption in the medullary collecting ducts.

The hypertonic interstitial fluid surrounding the collecting ducts of the kidney provides a high osmotic pressure for the removal of water. Transmembrane channels made of proteins called aquaporins are inserted in the plasma membrane greatly increasing its permeability to water. When open, an aquaporin channel allows 3 billion molecules of water to pass through each second. Insertion of aquaporin-2 channels requires signaling by vasopressin. Vasopressin binds to receptors (called V2 receptors) on the basolateral surface of the cells of the collecting ducts. Binding of the hormone triggers a rising level of cAMP within the cell. This "second messenger" initiates a chain of events culminating in the insertion of aquaporin-2 channels in the apical surface of the collecting duct cells. The aquaporins allow water to move out of the nephron, increasing the amount of water reabsorbed from the forming urine back into the bloodstream.

The main stimulus for the release of vasopressin from the pituitary gland is increased osmolality of the blood plasma. Anything that dehydrates the body, such as perspiring heavily increases the osmotic pressure of the blood and turns on the vasopressin to V2 receptor to aquaporin-2 pathway. As a result, as little as 0.5 liters/day of urine may remain of the original 180 liters/day of nephric filtrate. The concentration of salts in urine can be as high as four times that of the blood. If the blood should become too dilute, as would occur from drinking a large amount of water, vasopressin secretion is inhibited and the aquaporin-2 channels are taken back into the cell by endocytosis. The result is that a large volume of watery urine is formed with a salt concentration as little as one-fourth of that of the blood.

Decreased vasopressin release or decreased renal sensitivity to AVP leads to diabetes insipidus, a condition featuring hypernatremia (increased blood sodium concentration), polyuria (excess urine production), and polydipsia (thirst).

High levels of AVP secretion (syndrome of inappropriate antidiuretic hormone, SIADH) and resultant hyponatremia (low blood sodium levels) occurs in brain diseases and conditions of the lungs (Small cell lung carcinoma). In the perioperative period, the effects of surgical stress and some commonly used medications (e.g., opiates, syntocinon, antiemetics) lead to a similar state of excess vasopressin secretion. This may cause mild hyponatremia for several days.

Vasopressin agonists are used therapeutically in various conditions, and its long-acting synthetic analogue desmopressin is used in conditions featuring low vasopressin secretion, as well as for control of bleeding (in some forms of von Willebrand disease) and in extreme cases of bedwetting by children. Terlipressin and related analogues are used as vasoconstrictors in certain conditions. Vasopressin infusion has been used as a second line of management in septic shock patients not responding to high dose of inotropes (e.g., dopamine or norepinephrine). A vasopressin receptor antagonist is an agent that interferes with action at the vasopressin receptors. They can be used in the treatment of hyponatremia.

In one embodiment, the disclosure provides methods to select for conditionally active biologic recombinant or synthetic protein variants of proteins involved in the vasopressin response to be reversibly deactivated at normal physiological osmotic pressure, but reactivated at aberrant osmotic pressure in the blood. In another embodiment, variants of proteins involved in the vasopressin response are activated under hyponatremic conditions, but inactivated at normal serum sodium concentrations. In one aspect, hyponatremic conditions are those where serum sodium <135 mEq/L.

Cancer—Angiostatin

Angiostatin is a naturally occurring protein in several animal species. It acts as an endogenous angiogenesis inhibitor (i.e., it blocks the growth of new blood vessels). Angiostatin is able to suppress tumor cell growth and metastasis through inhibition of endothelial cell proliferation and migration. Angiostatin is a 38 kD fragment of plasmin (which is itself a fragment of plasminogen). Angiostatin comprises the kringles 1 to 3 of plasminogen. Angiostatin is produced, for example, by autolytic cleavage of plasminogen, involving extracellular disulfide bond reduction by phosphoglycerate kinase. Angiostatin can also be cleaved from plasminogen by different matrix metalloproteinases (MMPs) including MMP2, MMP12 and MMP9, and serine proteases (neutrophil elastase, prostate-specific antigen (PSA)). In vivo angiostatin inhibits tumor growth and keeps experimental metastasis in a dormant state. Angiostatin is elevated in animals with primary tumors and other inflammatory and degenerative diseases.

Angiostatin is known to bind many proteins including angiomotin and endothelial cell surface ATO synthase, but also integrins, annexin II, C-met receptor, NG2-proteoglycans, tissue-plasminogen activator, chondroitin sulfate glycoproteins, and CD26. One study shows that IL-12, a TH1 cytokine with potent antiangiogenic activity, is a mediator of angiostatin's activity. Albin"., J. Translational Medicine. Jan. 4, 2009, 7:5. Angiostatin binds and inhibits ATP synthase on the endothelial cell surface. ATP synthase also occurs on the surface of a variety of cancer cells. Tumor cell surface ATP synthase was found to be more active at low extracellular pH; a hallmark of tumor microenvironment. Angiostatin was found to affect tumor cell surface ATP synthase activity at acidic extracellular pH (pHe). At low extracellular pH, angiostatin was directly anti-tumorigenic. At low pH, angiostatin and anti-beta-subunit antibody induce intracellular acidification of A549 cancer cells, as well as a direct toxicity that is absent in tumor cells with low levels of extracellular ATP synthase. It was hypothesized that the mechanism of tumor cytotoxicity is dependent on intracellular pH deregulation due to inhibition of cell surface ATP synthase. Chi and Pizzo, "Angiostatin is directly cytotoxic to tumor cells at low extracellular pH: a mechanism dependent on cell surface-associated ATP synthase", Cancer Res., 2006, 66(2): 875-82.

In one embodiment, the disclosure provides a method for identification of conditionally active angiostatin variant which is less active than wild-type angiostatin at normal physiological blood pH, but exhibits enhanced activity at low pH. Low pH is defined as being less than normal physiological pH. In one aspect, low pH is less than about pH 7.2. In a particular aspect, low pH is about pH 6.7.

In one aspect, the conditionally active angiostatin variant can be formulated and utilized as an anticancer agent.

Enhancement of Tissue Permeability—Hyaluronidase

Hyaluronidases are a family of enzymes that degrade hyaluronic acid. By catalyzing the degradation of hyaluronic acid, a major constituent of the interstitial barrier, hyaluronidase lowers the viscosity of hyaluronic acid, thereby increasing tissue permeability. It is used in medicine in conjunction with drugs to speed their dispersion and delivery. The most common application is in ophthalmic surgery, used in combination with local anesthetics. Animal derived hyaluronidase include Hydase™ (PrimaPharm Inc.; Akorn Inc.), Vitrase (ISTA Pharmaceuticals) and Amphadase (Amphastar Pharmaceuticals). Human Recombinant Hyaluronidase is currently approved as an adjuvant to increase absorption of other drugs; hypodermocyclis (subcutaneous infusion of fluids); adjunct in subcutaneous urography to improve resorption of radioopaque agents. (Hylenex; Halozyme Therapeutics, Inc.; Baxter Healthcare Corp.) In one embodiment, hyaluronidase can serve as a wild-type protein (parent molecule) for preparation of a conditionally active biologic protein. Hyaluronidases may play a role in cancer metastasis and perhaps angiogenesis; therefore overexposure to these enzymes could be deleterious. In one aspect, a conditionally active biologic hyaluronidase protein would become irreversibly or reversibly inactivated at normal physiological temperature, but would be active at a level equal to or exceeding that of the wild-type hyaluronidase at certain temperature ranges below that of normal physiological temperature.

Autoimmune Diseases—Conditionally Active Biological Response Modifiers

Rheumatoid arthritis is an autoimmune disease characterized by aberrant immune mechanisms that lead to joint inflammation and swelling with progressive destruction of the joints. RA can also affect the skin, connective tissue and organs in the body. Traditional treatment includes non-steroidal anti-inflammatory drugs (NSAIDS), COX-2 inhibitors, and disease-modifying anti-rheumatic drugs (DMARDS) such as methotrexate. None of the traditional treatment regimes is ideal, especially for long term use.

Biological response modifiers, which target inflammatory mediators, offer a relatively new approach to the treatment of rheumatoid arthritis and other autoimmune diseases. Such biological response modifiers include antibodies, or active portions thereof, against various inflammatory mediators such as IL-6, IL-6 receptor, TNF-alpha, IL-23 and IL-12.

Some of the first biological response modifiers were medications targeting tumor necrosis factor alpha (TNF-a), a pro-inflammatory cytokine involved in the pathogenesis of RA. Several anti-TNF-alpha medications are currently marketed for the treatment of RA. For example, Enbrel® (etanercept, Amgen) is a TNF-alpha blocker. Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. Etanercept is produced in a Chinese hamster ovary (CHO) mammalian cell expression system. It consists of 934 amino acids and an apparent molecular weight of about 150 kilodaltons. Enbrel® is used to treat rheumatoid arthritis, psoriatic arthritis, ankylosing spondylitis and plaque psoriasis. Serious side effects of Enbrel® include infections including tuberculosis, fungal infection, bacterial or viral infection due to opportunistic pathogens. Sepsis can also occur. Lymphoma, or other malignancies have also been reported.

Remicade® (infliximab) is a chimeric anti-TNF-alpha IgGk1 monoclonal antibody composed of human constant and murine variable regions. Remicade is administered by intravenous injection and is used to treat rheumatoid arthritis, psoriasis, Crohn's disease, ulcerative colitis, and ankylosing spondylitis. Side effects of Remicade include serious infection or sepsis, and rarely certain T-cell lymphomas. Other side effects include hepatotoxicity, certain severe hematologic events, hypersensitivity reactions and certain severe neurological events.

Other biological response modifiers include humanized anti-interleukin-6 (IL-6) receptor antibodies. IL-6 is a cytokine that contributes to inflammation, swelling and joint damage in RA. One humanized anti-IL-6 receptor antibody, Actemra (tocilizumab, Roche), is approved by the FDA and European Commission to treat adult patients with rheumatoid arthritis. Actemra is also approved in Japan for treatment of RA and juvenile idiopathic arthritis (sJIA). Phase III studies showed that treatment with Actemra as a monotherapy, or a combination'with MTX or other DMARDs, reduced signs and symptoms of RA compared with other therapies. Actemra is a humanized anti-human IL-6 receptor monoclonal antibody that competitively blocks the binding of IL-6 to its receptor. Thus, it inhibits the proliferative effects of IL-6, which lead to synovial thickening and pannus formation in RA. Serious side effects of Actemra, include serious infections and hypersensitivity reactions including a few cases of anaphylaxis. Other side effects include upper respiratory tract infection, headache, nasopharyngitis, hypertension and increased ALT.

Another common autoimmune disease is psoriasis. An overactive immune system can lead to high levels of IL-12 and IL-23, two cytokine proteins that have been found in psoriatic skin plaques. IL-12 and IL-23 are involved in inflammatory and immune responses such as natural killer cell activation and CD4+ T-cell differentiation and activation.

One treatment for moderate or severe psoriasis involves subcutaneous injection of Stelara™ (ustekinumab, Centocor Ortho Biotech, Inc.) a humanized IgG1k monoclonal antibody against the p40 subunit of the IL-12 and IL-23 cytokines. Stelara has been shown to provide relief from certain symptoms associated with psoriatic plaques, such as plaque thickness, scaling and redness. The formulation for Stelara includes L-histidine and L-histidine monohydrochloride monohydrate, polysorbate 80, and sucrose in aqueous solution. Use of Stelara™ affects the immune system, and may increase chances of infection, including tuberculosis, and infections caused by bacteria, fungi or viruses; as well as increase the risk of certain types of cancer.

Side effects of the biological response modifiers are significant and are caused in part by high levels following injection into patients renders patients susceptible to serious infection or death. This is a major side effect associated with this important class of drugs. One challenge is avoiding the high initial level of activity from the dose of antibody required to provide a long treatment effect following injection.

In one embodiment, the disclosure provides a method to prepare a conditionally active biological response mediator, or fragment thereof, that avoids the high level of activity from the dose of antibody required to provide a long treatment effect following injection. The method of the disclosure can be used to design antibodies to inflammatory mediators such as IL-6, IL-6 receptor, TNF-alpha, IL-23 and IL-12 that are inactive at dosing conditions such as room temperature, but slowly refold (reversibly or irreversibly) at body temperature. These antibodies or fragments thereof would be inactive upon initial injection, but would refold or reactivate over a period of hours to days when exposed to blood following injection. This could allow higher dosing, and a longer half-life (or periods between dosing) with reduced side effects.

In one aspect, the disclosure provides a method for preparation of a conditionally active antibody to an inflammatory mediator, or fragment thereof, that is inactive at dosing conditions such as room temperature, but slowly refold (reversibly or irreversibly) at body temperature. The method comprises the following steps. Selecting an inflammatory mediator. Screening to identify an antibody to the inflammatory mediator via hybridoma. Humanizing the anti-inflammatory mediator antibody. Evolving the anti-inflammatory mediator antibody and screening differentially for binding at two or more conditions, for example, two or more temperature conditions such as at room temperature and at 37° C. or higher; selecting for mutations that are inactive at a first condition, relative to wild type, but show increased activity (e.g. binding) relative to the wild type antibody activity (binding) at a second condition. The up-mutants identified in the heavy and light changes are then recombined within the heavy and light chains, as well as through combinatorial association of the heavy and light chains. Screening of these recombined heavy and light chains is repeated at the two conditions, for example, room temperature and at 37° C. or higher. In addition, the recombined antibodies or fragments can be screened for activity and stability under storage and physiological conditions.

Alternatively, the wild-type antibody to the inflammatory mediator is a known antibody or variant or active fragment thereof.

In one aspect, the first and second conditions are selected from conditions of pH, osmotic pressure, osmolality, oxidation and electrolyte concentration. In another aspect, the inflammatory mediator is selected from IL-6, IL-6 receptor, TNF-alpha, IL-23 and IL-12.

In another aspect, the disclosure provides a method for preparation of a conditionally active antibody to IL-6, or fragment thereof, that is inactive at dosing conditions such as room temperature, but slowly refold (reversibly or irreversibly) at body temperature. The method comprises the following steps. Screening a fully human library for an antibody to IL-6. Evolving the IL-6 antibody and screening differentially for molecules at room temperature and at 37° C. or higher; selecting for mutations that are inactive at room temperature, relative to wild type, but show increased activity (e.g. binding) relative to the wild type antibody activity (binding). The up-mutants identified in the heavy and light changes are then recombined within the heavy and light chains, as well as through combinatorial association of the heavy and light chains. Screening of these recombined heavy and light chains is repeated at room temperature and the higher temperature. In addition, the recombined antibodies or fragments are tested for activity and stability under storage and physiological conditions.

The conditionally active anti-IL-6 antibodies thus identified and produced can be used in a method to treat an autoimmune disease, such as rheumatoid arthritis or psoriasis, by administration of an effective amount to a patient in need thereof, with a reduction in the severity of side effects compared to administration of a traditional biological response modifier anti-IL-6 antibody. One advantage of this method is that it allows for smoothing or leveling of the drug quantity over the period of treatment relative to the current high level of biological response modifier drug followed by half-life clearance over weeks or months.

One or more mutagenesis techniques are employed to evolve the DNA which encodes the wild-type protein to create a library of mutant DNA; the mutant DNA is expressed to create a library of mutant proteins; and the library is subjected to a screening assay under a normal physiological condition and under one or more aberrant conditions. Conditionally active biologic proteins are selected from those proteins which exhibit both (a) a decrease in activity in the assay at the normal physiological condition compared to the wild-type protein, and (b) an increase in activity in the assay under the aberrant condition compared to the wild-type protein. Alternatively, conditionally active biologic proteins are selected from those proteins which exhibit changes in activity, reversibly or irreversibly, in two or more different physiological conditions.

Generation of Evolved Molecules from Parent Molecule

Mirac Proteins can be generated through a process of mutagenesis and screening for individual mutations for a reduction in activity at the wild-type condition with activity at non wild-type conditions remaining the same or better than the activity at the wild-type condition.

The disclosure provides for a method for generating a nucleic acid variant encoding a polypeptide having enzyme activity, wherein the variant has an altered biological activity from that which naturally occurs, the method comprising (a) modifying the nucleic acid by (i) substituting one or more nucleotides for a different nucleotide, wherein the nucleotide comprises a natural or non-natural nucleotide; (ii) deleting one or more nucleotides, (iii) adding one or more nucleotides, or (iv) any combination thereof. In one aspect, the non-natural nucleotide comprises inosine. In another aspect, the method further comprises assaying the polypeptides encoded by the modified nucleic acids for altered enzyme activity, thereby identifying the modified nucleic acid(s) encoding a polypeptide having altered enzyme activity. In one aspect, the modifications of step (a) are made by PCR, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis, ligase chain reaction, in vitro mutagenesis, ligase chain reaction, oligonuclteotide synthesis, any DNA-generating technique and any combination thereof. In another aspect, the method further comprises at least one repetition of the modification step (a).

The disclosure further provides a method for making a polynucleotide from two or more nucleic acids, the method comprising: (a) identifying regions of identity and regions of diversity between two or more nucleic acids, wherein at least one of the nucleic acids comprises a nucleic acid of the disclosure; (b) providing a set of oligonucleotides which correspond in sequence to at least two of the two or more nucleic acids; and, (c) extending the oligonucleotides with a polymerase, thereby making the polynucleotide.

Any technique of mutagenesis can be employed in various embodiments of the disclosure. Stochastic or random mutagenesis is exemplified by a situation in which a parent molecule is mutated (modified or changed) to yield a set of progeny molecules having mutation(s) that are not predetermined. Thus, in an in vitro stochastic mutagenesis reaction, for example, there is not a particular predetermined product whose production is intended; rather there is an uncertainty—hence randomness—regarding the exact nature of the mutations achieved, and thus also regarding the products generated. Stochastic mutagenesis is manifested in processes such as error-prone PCR and stochastic shuffling, where the mutation(s) achieved are random or not predetermined. The variant forms can be generated by error-prone transcription, such as an error-prone PCR or use of a polymerase which lacks proof-reading activity (see, Liao (1990) Gene 88:107-111), of the first variant form, or, by replication of the first form in a mutator strain (mutator host cells are discussed in further detail below, and are generally well known). A mutator strain can include any mutants in any organism impaired in the functions of mismatch repair. These include mutant gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small compound or an expressed antisense RNA, or other techniques. Impairment can be of the genes noted, or of homologous genes in any organism.

Current mutagenesis methods in widespread use for creating alternative proteins from a starting molecule are oligonucleotide-directed mutagenesis technologies, error-prone polymerase chain reactions (error-prone PCR) and cassette mutagenesis, in which the specific region to be optimized is replaced with a synthetically mutagenized oligonucleotide. In these cases, a number of mutant sites are generated around certain sites in the original sequence.

In oligonucleotide-directed mutagenesis, a short sequence is replaced with a synthetically mutagenized oligonucleotide. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into E. coli and propagated as a pool or library of hybrid plasmids.

Error-prone PCR uses low-fidelity polymerization conditions to introduce a low level of point mutations randomly over a long sequence. In a mixture of fragments of unknown sequence, error-prone PCR can be used to mutagenize the mixture.

In cassette mutagenesis, a sequence block of a single template is typically replaced by a (partially) randomized sequence. Reidhaar-Olson J F and Sauer R T: Combinatorial cassette mutagenesis as a probe of the informational content of protein sequences. Science 241(4861):53-57, 1988.

Alternatively, any technique of non-stochastic or non-random mutagenesis can be employed in various embodiments of the disclosure. Non-stochastic mutagenesis is exemplified by a situation in which a parent molecule is mutated (modified or changed) to yield a progeny molecule having one or more predetermined mutations. It is appreciated that the presence of background products in some quantity is a reality in many reactions where molecular processing occurs, and the presence of these background products does not detract from the non-stochastic nature of a mutagenesis process having a predetermined product. Site-saturation mutagenesis and synthetic ligation reassembly, are examples of mutagenesis techniques where the exact chemical structure(s) of the intended product(s) are predetermined.

One method of site-saturation mutagenesis is disclosed in U.S. patent application publication 2009/0130718, which is incorporated herein by reference. This method provides a set of degenerate primers corresponding to codons of a template polynucleotide, and performs polymerase elongation to produce progeny polynucleotides, which contain sequences corresponding to the degenerate primers. The progeny polynucleotides can be expressed and screened for directed evolution. Specifically, this is a method for producing a set of progeny polynucleotides, comprising the steps of (a) providing copies of a template polynucleotide, each comprising a plurality of codons that encode a template polypeptide sequence; and (b) for each codon of the template polynucleotide, performing the steps of (1) providing a set of degenerate primers, where each primer comprises a degenerate codon corresponding to the codon of the template polynucleotide and at least one adjacent sequence that is homologous to a sequence adjacent to the codon of the template polynucleotide; (2) providing conditions allowing the primers to anneal to the copies of the template polynucleotides; and (3) performing a polymerase elongation reaction from the primers along the template; thereby producing progeny polynucleotides, each of which contains a sequence corresponding to the degenerate codon of the annealed primer; thereby producing a set of progeny polynucleotides.

Site-saturation mutagenesis relates to the directed evolution of nucleic acids and screening of clones containing the evolved nucleic acids for resultant activity(ies) of interest, such nucleic acid activity(ies) &/or specified protein, particularly enzyme, activity(ies) of interest.

Mutagenized molecules provided by this technique may have chimeric molecules and molecules with point mutations, including biological molecules that contain a carbohydrate, a lipid, a nucleic acid, &/or a protein component, and specific but non-limiting examples of these include antibiotics, antibodies, enzymes, and steroidal and non-steroidal hormones.

Site saturation mutagenesis relates generally to a method of: 1) preparing a progeny generation of molecule(s) (including a molecule that is comprised of a polynucleotide sequence, a molecule that is comprised of a polypeptide sequence, and a molecule that is comprised in part of a polynucleotide sequence and in part of a polypeptide sequence), that is mutagenized to achieve at least one point mutation, addition, deletion, &/or chimerization, from one or more ancestral or parental generation template(s); 2) screening the progeny generation molecule(s)—preferably using a high throughput method—for at least one property of interest (such as an improvement in an enzyme activity or an increase in stability or a novel chemotherapeutic effect); 3) optionally obtaining &/or cataloguing structural &/or and functional information regarding the parental &/or progeny generation molecules; and 4) optionally repeating any of steps 1) to 3).

In site saturation mutagenesis, there is generated (e.g. from a parent polynucleotide template)—in what is termed "codon site-saturation mutagenesis"—a progeny generation of polynucleotides, each having at least one set of up to three contiguous point mutations (i.e. different bases comprising a new codon), such that every codon (or every family of degenerate codons encoding the same amino acid) is represented at each codon position. Corresponding to—and encoded by—this progeny generation of polynucleotides, there is also generated a set of progeny polypeptides, each having at least one single amino acid point mutation. In a preferred aspect, there is generated—in what is termed "amino acid site-saturation mutagenesis"—one such mutant polypeptide for each of the 19 naturally encoded polypeptide-forming alpha-amino acid substitutions at each and every amino acid position along the polypeptide. This yields—for each and every amino acid position along the parental polypeptide—a total of 20 distinct progeny polypeptides including the original amino acid, or potentially more than 21 distinct progeny polypeptides if additional amino acids are used either instead of or in addition to the 20 naturally encoded amino acids.

Other mutagenesis techniques can also be employed which involve recombination and more specifically a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

In another aspect, mutagenesis techniques exploit the natural property of cells to recombine molecules and/or to mediate reductive processes that reduce the complexity of sequences and extent of repeated or consecutive sequences possessing regions of homology.

Various mutagenesis techniques can be used alone or in combination to provide a method for generating hybrid polynucleotides encoding biologically active hybrid polypeptides with enhanced activities. In accomplishing these and other objects, there has been provided, in accordance with one aspect of the disclosure, a method for introducing polynucleotides into a suitable host cell and growing the host cell under conditions that produce a hybrid polynucleotide.

Chimeric genes have been made by joining 2 polynucleotide fragments using compatible sticky ends generated by restriction enzyme(s), where each fragment is derived from a separate progenitor (or parental) molecule. Another example is the mutagenesis of a single codon position (i.e. to achieve a codon substitution, addition, or deletion) in a parental polynucleotide to generate a single progeny polynucleotide encoding for a single site-mutagenized polypeptide.

Further, in vivo site specific recombination systems have been utilized to generate hybrids of genes, as well as random methods of in vivo recombination, and recombination between homologous but truncated genes on a plasmid. Mutagenesis has also been reported by overlapping extension and PCR.

Non-random methods have been used to achieve larger numbers of point mutations and/or chimerizations, for example comprehensive or exhaustive approaches have been used to generate all the molecular species within a particular grouping of mutations, for attributing functionality to specific structural groups in a template molecule (e.g. a specific single amino acid position or a sequence comprised of two or more amino acids positions), and for categorizing and comparing specific grouping of mutations.

Any of these or other methods of evolving can be employed in the present disclosure to generate a new population of molecules (library) from one or more parent molecules.

Once formed, the constructs may, or may not be size fractionated on an agarose gel according to published protocols, inserted into a cloning vector, and transfected into an appropriate host cell.

Expression of Evolved Molecules

Once a library of mutant molecules is generated, DNA can be expressed using routine molecular biology techniques. Thus, protein expression can be directed using various known methods.

For example, briefly, a wild type gene can be evolved using any variety of random or non-random methods such as those indicated herein. Mutant DNA molecules are then digested and ligated into vector DNA, such as plasmid DNA using standard molecular biology techniques. Vector DNA containing individual mutants is transformed into bacteria or other cells using standard protocols. This can be done in an individual well of a multi-well tray, such as a 96-well tray for high throughput expression and screening. The process is repeated for each mutant molecule.

Polynucleotides selected and isolated as described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (e.g. Ecker and Davis, 1986, Inhibition of gene expression in plant cells by expression of antisense RNA, Proc Natl Acad Sci USA, 83:5372-5376).

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present disclosure.

The DNA sequence in the expression vector is operatively linked to an appropriate expression control sequence(s) (promoter) to direct RNA synthesis. Particular named bacterial promoters include lad, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Therefore, in another aspect of the disclosure, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

In one aspect, the host organism or cell comprises a gram negative bacterium, a gram positive bacterium or a eukaryotic organism. In another aspect of the disclosure, the gram negative bacterium comprises *Escherichia coli*, or *Pseudomonas fluorescens*. In another aspect of the disclosure, the gram positive bacterium comprise *Streptomyces diversa, Lactobacillus gasseri, Lactococcus lactis, Lactococcus cremoris*, or *Bacillus subtilis*. In another aspect of the disclosure, the eukaryotic organism comprises *Saccharomyces cerevisiae, Schizosaccharomyces pombe, Pichia pastoris, Kluyveromyces lactis, Hansenula plymorpha*, or *Aspergillus niger*. As representative examples of appropriate hosts, there may be mentioned: bacterial cells, such as *E. coli, Streptomyces, Salmonella typhimurium*; fungal cells, such as yeast; insect cells such as Drosophila S2 and Spodoptera Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The cells are then propagated and "reductive reassortment" is effected. The rate of the reductive reassortment process may be stimulated by the introduction of DNA damage if desired. In vivo reassortment is focused on "inter-molecular" processes collectively referred to as "recombination" which in bacteria, is generally viewed as a "RecA-dependent" phenomenon. The disclosure can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process. The end result is a reassortment of the molecules into all possible combinations.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

Protein expression can be induced by a variety of known methods, and many genetic systems have been published for induction of protein expression. For example, with appropriate systems, the addition of an inducing agent will induce protein expression. Cells are then pelleted by centrifugation and the supernatant removed. Periplasmic protein can be enriched by incubating the cells with DNAse, RNAse, and lysozyme. After centrifugation, the supernatant, containing the new protein, is transferred to a new multi-well tray and stored prior to assay.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The clones which are identified as having the desired activity may then be sequenced to identify the polynucleotide sequence encoding an enzyme having the enhanced activity.

The polypeptides that are identified from such libraries can be used for therapeutic, diagnostic, research and related purposes, and/or can be subjected to one or more additional cycles of shuffling and/or selection. The disclosure provides for a fragment of the conditionally active biologic protein which is at least 10 amino acids in length, and wherein the fragment has activity.

The disclosure provides for a codon-optimized polypeptide or a fragment thereof, having enzyme activity, wherein the codon usage is optimized for a particular organism or cell. Narum et al., "Codon optimization of gene fragments encoding Plasmodium falciparum merzoite proteins enhances DNA vaccine protein expression and immunogenicity in mice". Infect. Imam. 2001 December, 69(12): 7250-3 describes codon-optimization in the mouse system. Outchkourov et al., "Optimization of the expression of Equistatin in Pichia pastoris, protein expression and purification", Protein Expr. Purif. 2002 February; 24(1):18-24 describes codon-optimization in the yeast system. Feng et al., "High level expression and mutagenesis of recombinant human phosphatidylcholine transfer protein using a synthetic gene: evidence for a C-terminal membrane binding domain" Biochemistry 2000 Dec. 19, 39(50):15399-409 describes codon-optimization in *E. coli*. Humphreys et al., "High-level periplasmic expression in *Escherichia coli* using a eukaryotic signal peptide: importance of codon usage at the 5' end of the coding sequence", Protein Expr. Purif. 2000 Nov. 20(2):252-64 describes how codon usage affects secretion in *E. coli*.

The evolution of a conditionally active biologic protein can be aided by the availability of a convenient high throughput screening or selection process.

Once identified, polypeptides and peptides of the disclosure can be synthetic, or be recombinantly generated polypeptides. Peptides and proteins can be recombinantly expressed in vitro or in vivo. The peptides and polypeptides of the disclosure can be made and isolated using any method known in the art. Polypeptide and peptides of the disclosure can also be synthesized, whole or in part, using chemical methods well known in the art. See e.g., Caruthers (1980) "New chemical methods for synthesizing polynucleotides", Nucleic Acids Res. Symp. Ser. 215-223; Horn (1980), "Synthesis of oligonucleotides on cellulose. Part II: design and synthetic strategy to the synthesis of 22 oligodeoxynucleotides coding for Gastric Inhibitory Polypeptide (GIP) 1'", Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) "A strategy for a convergent synthesis of N-linked glycopeptides on a solid support", Science 269: 202; Merrifield (1997) "Concept and early development of solid-phase peptide synthesis", Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the disclosure can also be glycosylated. The glycosylation can be added post-translationally either chemically or by cellular biosynthetic mechanisms, wherein the latter incorporates the use of known glycosylation motifs, which can be native to the sequence or can be added as a peptide or added in the nucleic acid coding sequence. The glycosylation can be O-linked or N-linked.

The peptides and polypeptides of the disclosure, as defined above, include all "mimetic" and "peptidomimetic" forms. The terms "mimetic" and "peptidomimetic" refer to a synthetic chemical compound which has substantially the same structural and/or functional characteristics of the polypeptides of the disclosure. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the disclosure which are conservative variants, routine experimentation will determine whether a mimetic is within the scope of the disclosure, i.e., that its structure and/or function is not substantially altered.

Polypeptide mimetic compositions of the disclosure can contain any combination of non-natural structural components. In alternative aspect, mimetic compositions of the disclosure include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the disclosure can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(.dbd.O)—CH.sub.2- for —C(.dbd.O)—NH—), aminomethylene (CH.sub.2-NH), ethylene, olefin (CH.dbd.CH), ether (CH.sub.2-O), thioether (CH.sub.2-S), tetrazole (CN.sub.4-), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, N.Y.).

A polypeptide of the disclosure can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1,-2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D-or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylanines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4,pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethyl-procarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the disclosure can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The disclosure also provides methods for modifying the polypeptides of the disclosure by either natural processes, such as post-translational processing (e.g., phosphorylation, acylation, etc), or by chemical modification techniques. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, PEGylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W. H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the disclosure. Such methods have been known in the art since the early 1960's (Merrifield, R. B., "Solid-phase synthesis.I. The synthesis of a tetrapeptide", J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al., "Use of peptide synthesis to probe viral antigens for epitopes to a resolution of a single amino acid," Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the disclosure, either by direct synthesis or by synthesis of a series of fragments that can be coupled using other known techniques.

The synthetic polypeptide or fragment thereof can be recovered and purified by known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The disclosure provides for a conditionally active protein variant preparation or formulation which comprises at least one of the protein variants, wherein the preparation is liquid or dry. The protein formulation optionally includes a buffer, cofactor, second or additional protein, or one or more excipients. In one aspect the formulation is utilized as a therapeutic conditionally active biologic protein which is active under aberrant or non-physiological conditions, but less active or inactive under normal physiological conditions of, e.g., temperature, pH, or osmotic pressure, oxidation or osmolality.

Standard purification techniques can be employed for either recombinant or synthetic conditionally active biologic proteins.

Screening of Mutants to Identify Reversible or Non-Reversible Mutants

Identifying desirable molecules is most directly accomplished by measuring protein activity at the permissive condition and the wild type condition. The mutants with the largest ratio of activity (permissive/wild type) can then be selected and permutations of the point mutations are generated by combining the individual mutations using standard methods. The combined permutation protein library is then screened for those proteins displaying the largest differential activity between the permissive and wild type condition.

Activity of supernatants can be screened using a variety of methods, for example using high throughput activity assays, such as fluorescence assays, to identify protein mutants that are sensitive at whatever characteristic one desires (temperature, pH, etc). For example, to screen for temporally sensitive mutants, the enzymatic or antibody activity of each individual mutant is determined at lower temperatures (such as 25 degrees Celsius), and at temperatures which the original protein functions (such as 37 degrees Celsius), using commercially available substrates. Reactions can initially be performed in a multi well assay format, such as a 96-well assay, and confirmed using a different format, such as a 14 ml tube format.

The disclosure further provides a screening assay for identifying a enzyme, the assay comprising: (a) providing a plurality of nucleic acids or polypeptides; (b) obtaining polypeptide candidates to be tested for enzyme activity from the plurality; (c) testing the candidates for enzyme activity; and (d) identifying those polypeptide candidates which exhibit elevated enzyme activity under aberrant or non-physiological conditions, and decreased enzyme activity compared to the wild-type enzyme protein under normal physiological conditions of, e.g., temperature, pH, oxidation, osmolality, electrolyte concentration or osmotic pressure.

In one aspect, the method further comprises modifying at least one of the nucleic acids or polypeptides prior to testing the candidates for conditional biologic activity. In another aspect, the testing of step (c) further comprises testing for improved expression of the polypeptide in a host cell or host organism. In a further aspect, the testing of step (c) further comprises testing for enzyme activity within a pH range from about pH 3 to about pH 12. In a further aspect, the testing of step (c) further comprises testing for enzyme activity within a pH range from about pH 5 to about pH 10. In a further aspect, the testing of step (c) further comprises testing for enzyme activity within a pH range from about pH 6 to about pH 8. In a further aspect, the testing of step (c) further comprises testing for enzyme activity at pH 6.7 and pH 7.5. In another aspect, the testing of step (c) further comprises testing for enzyme activity within a temperature range from about 4 degrees C. to about 55 degrees C. In another aspect, the testing of step (c) further comprises testing for enzyme activity within a temperature range from about 15 degrees C. to about 47 degrees C. In another aspect, the testing of step (c) further comprises testing for enzyme activity within a temperature range from about 20 degrees C. to about 40 degrees C. In another aspect, the testing of step (c) further comprises testing for enzyme activity at the temperatures of 25 degrees C. and 37 degrees C. In another aspect, the testing of step (c) further comprises testing for enzyme activity under normal osmotic pressure, and aberrant (positive or negative) osmotic pressure. In another aspect, the testing of step (c) further comprises testing for enzyme activity under normal electrolyte concentration, and aberrant (positive or negative) electrolyte concentration. The electrolyte concentration to be tested is selected from one of calcium, sodium, potassium, magnesium, chloride, bicarbonate and phosphate concentration. In another aspect, the testing of step (c) further comprises testing for enzyme activity which results in a stabilized reaction product.

In another aspect, the disclosure provides for a purified antibody that specifically binds to the polypeptide of the disclosure or a fragment thereof, having enzyme activity. In one aspect, the disclosure provides for a fragment of the antibody that specifically binds to a polypeptide having enzyme activity.

Antibodies and Antibody-Based Screening Methods

The disclosure provides isolated or recombinant antibodies that specifically bind to an enzyme of the disclosure. These antibodies can be used to isolate, identify or quantify the enzymes of the disclosure or related polypeptides. These antibodies can be used to isolate other polypeptides within the scope the disclosure or other related enzymes. The antibodies can be designed to bind to an active site of an enzyme. Thus, the disclosure provides methods of inhibiting enzymes using the antibodies of the disclosure.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the disclosure. Alternatively, the methods of the disclosure can be used to modify the structure of an antibody produced by a cell to be modified, e.g., an antibody's affinity can be increased or decreased. Furthermore, the ability to make or modify antibodies can be a phenotype engineered into a cell by the methods of the disclosure.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) "Continuous cultures of fused cells secreting antibody of predefined specificity", Nature 256: 495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) "Designing and optimizing library selection strategies for generating high-affinity antibodies", Trends Biotechnol. 15:62-70; and Katz (1997) "Structural and mechanistic determinants of affinity and specificity of ligands discovered or engineered by phage display", Annu. Rev. Biophys. Biomol. Struct. 26:27-45.

Polypeptides or peptides can be used to generate antibodies which bind specifically to the polypeptides, e.g., the enzymes, of the disclosure. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the disclosure.

In immunoaffinity procedures, the antibody is attached to a solid support, such as a bead or other column matrix. The protein preparation is placed in contact with the antibody under conditions in which the antibody specifically binds to one of the polypeptides of the disclosure. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the disclosure can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the disclosure. Alternatively, transgenic mice may be used to express humanized antibodies to these polypeptides or fragments thereof. Antibodies generated against the polypeptides of the disclosure may be used in screening for similar polypeptides (e.g., enzymes) from other organisms and samples. In such techniques, polypeptides from the organism are contacted with the antibody and those polypeptides which specifically bind the antibody are detected. Any of the procedures described above may be used to detect antibody binding.

Screening Methodologies and "On-Line" Monitoring Devices

In practicing the methods of the disclosure, a variety of apparatus and methodologies can be used to in conjunction with the polypeptides and nucleic acids of the disclosure, e.g., to screen polypeptides for enzyme activity, to screen compounds as potential modulators, e.g., activators or inhibitors, of an enzyme activity, for antibodies that bind to a polypeptide of the disclosure, for nucleic acids that hybridize to a nucleic acid of the disclosure, to screen for cells expressing a polypeptide of the disclosure and the like.

Arrays, or "Biochips"

Nucleic acids or polypeptides of the disclosure can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the disclosure. For example, in one aspect of the disclosure, a monitored parameter is transcript expression of an enzyme gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the disclosure. Polypeptide arrays" can also be used to simultaneously quantify a plurality of proteins. The present disclosure can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the disclosure, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) "Gene chips: Array of hope for understanding gene regulation", Curr. Biol. 8:R171-R174; Schummer (1997) "Inexpensive Handheld Device for the Construction of High-Density Nucleic Acid Arrays", Biotechniques 23:1087-1092; Kern (1997) "Direct hybridization of large-insert genomic clones on high-density gridded cDNA filter arrays", Biotechniques 23:120-124; Solinas-Toldo (1997) "Matrix-Based Comparative Genomic Hybridization: Biochips to Screen for Genomic Imbalances", Genes, Chromosomes & Cancer 20:399-407; Bowtell (1999) "Options Available—From Start to Finish—for Obtaining Expression Data by Microarray", Nature Genetics Supp. 21:25-32. See also published U.S. patent applications Nos. 20010018642; 20010019827; 20010016322; 20010014449; 20010014448; 20010012537; 20010008765.

Capillary Arrays

Capillary arrays, such as the GIGAMATRIX™ Diversa Corporation, San Diego, Calif., can be used in the methods of the disclosure. Nucleic acids or polypeptides of the disclosure can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the disclosure. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample. A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube. The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Pharmaceutical Compositions

The present disclosure provides at least one composition comprising (a) a conditionally active biologic protein; and (b) a suitable carrier or diluent. The present disclosure also provides at least one composition comprising (a) a conditionally active biologic protein encoding nucleic acid as described herein; and (b) a suitable carrier or diluent. The carrier or diluent can optionally be pharmaceutically acceptable, according to known carriers or diluents. The composition can optionally further comprise at least one further compound, protein or composition.

The conditionally active biologic protein may be in the form of a pharmaceutically acceptable salt. Pharmaceutically acceptable salts means which can be generally used as salts of an therapeutic protein in pharmaceutical industry, including for example, salts of sodium, potassium, calcium and the like, and amine salts of procaine, dibenzylamine, ethylenediamine, ethanolamine, methylglucamine, taurine, and the like, as well as acid addition salts such as hydrochlorides, and basic amino acids and the like.

The present disclosure further provides at least one conditionally active biologic protein method or composition, for administering a therapeutically effective amount to modulate or treat at least one parent molecule related condition in a cell, tissue, organ, animal or patient and/or, prior to, subsequent to, or during a related condition, as known in the art and/or as described herein. Thus, the disclosure provides a method for diagnosing or treating a condition associated with the wild-type protein in a cell, tissue, organ or animal, comprising contacting or administering a composition comprising an effective amount of at least one conditionally active biologic protein of the disclosure with, or to, the cell, tissue, organ or animal. The method can optionally further comprise using an effective amount of 0.001-50 mg/kilogram of a conditionally active biologic protein of the disclosure to the cells, tissue, organ or animal. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further comprise administering, prior, concurrently, or after the conditionally active biologic protein contacting or administering at least one composition comprising an effective amount of at least one compound or protein selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, or an anti-proliferative agent.

The present disclosure further provides at least one conditionally active biologic protein method for diagnosing at least one wild-type protein related condition in a cell, tissue, organ, animal or patient and/or, prior to, subsequent to, or during a related condition, as known in the art and/or as described herein.

Pharmaceutically acceptable carriers are determined in part by the particular composition being administered, as well as by the particular method used to administer the composition. Accordingly, there is a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of conditionally active biologic protein in these formulations can vary widely, and will be selected primarily based on fluid volumes, viscosities, body weight and the like in accordance with the particular mode of administration selected and the patient's needs.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Pharmaceutical compositions and formulations of the invention for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscannellose sodium, talc, magnesium stearate, stearic acid, and other excipients, colorants, fillers, binders, diluents, buffering agents, moistening agents, preservatives, flavoring agents, dyes, disintegrating agents, and pharmaceutically acceptable carriers.

The invention provides aqueous suspensions comprising a conditionally active biologic protein, in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the conditionally active biologic protein, when administered orally, must be protected from digestion. This is typically accomplished either by complexing the conditionally active biologic protein with a composition to render it resistant to acidic and enzymatic hydrolysis or by packaging the conditionally active biologic protein in an appropriately resistant carrier such as a liposome. Means of protecting proteins from digestion are well known in the art. The pharmaceutical compositions can be encapsulated, e.g., in liposomes, or in a formulation that provides for slow release of the active ingredient.

The packaged conditionally active biologic protein, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like. Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Dermal or topical delivery compositions of the invention may include in addition to a conditionally active biologic protein, a pharmaceutically acceptable carrier in a cream, ointment, solution or hydrogel formulation, and other compounds so long as the added component does not deleteriously affect delivery of the therapeutic protein. Conventional pharmaceutically acceptable emulsifiers, surfactants, suspending agents, antioxidants, osmotic enhancers, extenders, diluents and preservatives may also be added. Water soluble polymers can also be used as carriers.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. In one aspect, parenteral modes of administration are preferred methods of administration for compositions comprising a conditionally active biologic protein. The compositions may conveniently be administered in unit dosage form and may be prepared by any of the methods well-known in the pharmaceutical art, for example as described in Remington's Pharmaceutical Sciences, Mack Publishing Co. Easton Pa., $18^{th}$ Ed., 1990. Formulations for intravenous administration may contain a pharmaceutically acceptable carrier such as sterile water or saline, polyalkylene glycols such as polyethylene glycol, oils of vegetable origin, hydrogenated naphthalenes and the like. Also see and adapt the description in U.S. Pat. No. 4,318,905.

The formulations of packaged compositions comprising a conditionally active biologic protein can be presented in unit-dose or multi-dose sealed containers, such as ampoules and vials. Injection solutions and suspensions can be prepared from sterile powders, granules, and tablets of the kind previously described.

The present disclosure also provides at least one conditionally active biologic protein composition, device and/or method of delivery for diagnosing of at least one wild-type protein related condition, according to the present disclosure.

Also provided is a composition comprising at least one conditionally active biologic protein and at least one pharmaceutically acceptable carrier or diluent. The composition can optionally further comprise an effective amount of at least one compound or protein selected from at least one of a detectable label or reporter, a cytotoxic or other anti-cancer agent, an anti-metabolite such as methotrexate, an anti-proliferative agent, a cytokine, or a cytokine antagonist, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog.

Also provided is a medical device, comprising at least one conditionally active biologic protein of the disclosure, wherein the device is suitable to contacting or administering the at least one conditionally active biologic protein by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the disclosure provides a kit comprising at least one conditionally active biologic protein or fragment of the disclosure in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent. In one aspect, in the kit, the concentration of conditionally active biologic protein or specified portion or variant in the first container is reconstituted to a concentration of about 0.1 mg/ml to about 500 mg/ml with the contents of the second container. In another aspect, the second container further comprises an isotonicity agent. In another aspect, the second container further comprises a physiologically acceptable buffer. In one aspect, the disclosure provides a method of treating at least one wild-type protein mediated condition, comprising administering to a patient in need thereof a formulation provided in a kit and reconstituted prior to administration.

Also provided is an article of manufacture for human pharmaceutical or diagnostic use, comprising packaging material and a container comprising a solution or a lyophilized form of at least one conditionally active biologic protein of the present disclosure. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The present disclosure further provides any disclosure described herein.

Example 1

General Description of a Multiwall Assay (for example, 96-well assay) for Temperature Mutants Fluorescent substrate is added to each well of a multiwall plate, at both wild-type and new, lower reaction temperatures (for example, either 37° C. or 25° C. as mentioned above) for an appropriate time period. Fluorescence is detected by measuring fluorescence in a fluorescent plate reader at appropriate excitation and emission spectra (for example, 320 nm exitation/405 nm emission). Relative fluorescence units (RFU) are determined. Supernatant from wild type molecule and plasmid/vector transformed cells are used as positive and negative controls. Duplicate reactions are performed for each sample, reaction temperature, and positive and negative control.

Mutants that are active at the lower temperature (for example, the mutants active at 25° C.) and that have a decrease in activity at the wild type temperature (for example, a 10%, 20%, 30%, 40% or more decrease in activity at 37° C.), thus having a ratio of activities greater than or equal to about 1.1 or more (e.g., the ratio of the activities at 25° C. or 37° C. (25° C/37° C.) is greater than or equal to 1.1 or more), can be deemed to be putative primary temperature sensitive hits. These putative primary temperature sensitive hits can then be rescreened, using the same assay, to confirm any primary hits.

Example 2

General Description of a Different Assay Format for Confirmation of Activity (for Example, a 14-mL Assay) for Temperature Mutants Mutants that are identified as temperature sensitive primary hits are expressed in 14 ml culture tubes and their enzymatic activity is measured at wild type (for example, 37° C.) and the lower temperature (for example, 25° C.). Protein is expressed and purified as described above for the multiwall format, with the exception that the expression is performed in different format (14 ml tubes) rather than the multiwall (96-well plate) format.

Each mutant supernatant is transferred to a multiwall plate, for example a 96-well microplate. Fluorescent substrate is added to each tube at the indicated reaction temperatures (wild-type, lower temperature) for a required period of time. Wild-type molecules are used as a positive control and supernatant from cells transformed with only vector is used as a negative control. Fluorescence is detected by measuring fluorescence in a fluorescent plate reader at the appropriate emission spectra (for example, 320 nm exitation/405 nm emission). Relative fluorescence units (RFU) are determined. Duplicate reactions can are performed for each sample, reaction temperature, and positive and negative control.

Mutants that are active at the lower temperatures (for example, 25° C.) but that demonstrate at least a 30% or more decreased activity at wild type (for example, 37° C.), thus have a ratio of activity at lower temperature (for example, 25° C.) to wild type temperature (for example, 37° C.) equal to or greater than 1.5, are identified as temperature sensitive hits.

The activities of mutants at the lower temperature (for example 25° C.) are compared to the activity of the wild-type molecule at the wild-type temperature (for example 37° C.). If molecules are more active than the wild-type molecules at the lower temperature (for example 25° C.), as indicated by a residual activity >1, preferably 2 or greater than 2, and if the mutants demonstrate an overall decrease in activity when compared to the wild-type molecule at the wild-type temperature (37° C.), the phenotype of the mutants as temperature sensitive mutants can be confirmed.

Example 3

General Description of Further Evolution of Hits Discovered

If desired, a new, combinatorial variant library is generated from all or selected mutant hits previously identified. The new library can be designed to contain every possible combination of amino acid variants for each of the selected mutants, and rescreened as described for new hits.

Example 4

General Description of Reversibility of Enzymatic Activity Following Decrease in Temperature Temperature sensitive, evolved mutants can be further assayed to determine whether enzymatic activity at lower temperatures (for example, 25° C.) is reversible or irreversible by exposing the mutants to elevated temperatures followed by a return to the lower temperature (for example, 25° C.). The temperature sensitive mutants are expressed in any desired format, for example in 14 ml culture tubes, as briefly described. The mutants are tested for their activities under several conditions, including the wild-type temperature (for example, 37° C.) as well as other temperatures, and subsequently re-exposure to the requisite lower temperature of (25° C. for example). Mutants that are active at lower temperatures, show decreased activity when raised to higher or wild-type temperatures (i.e., the ratio of the activities at lower to higher temperatures is equal to or greater than 1, 1.5, or 2 or higher), and exhibit a baseline activity when lowered again to the lower temperature are scored as "Reversible Hits". Mutants that are active at the lower temperature, show decreased activity when raised to higher or wild-type temperatures (i.e., the ratio of the activities at the lower to higher temperatures is equal to or greater than 1, 1.5 or 2 or higher), and exhibit at least the same amount of decreased activity when lowered again to the lower temperature are scored as "Irreversible Hits".

Example 5

Materials and Methods to Screen for Conditionally Active Angiostatin Variants

Materials and methods to screen for conditionally active angiostatin variants can be adapted from Chi and Pizzo, "Angiosatin is directly cytotoxic to tumor cells at low extracellular pH: a mechanism dependent on cell surface-associated ATP synthase", Cancer Res. 2006; 66(2):875-882, which is incorporated herein by reference.

Materials. Wild-type angiostatin kringles 1 to 3, derived from human plasminogen, can be obtained from Calbiochem (Darmstadt, Germany) and reconstituted in sterile PBS. Polyclonal antibodies directed against the catalytic beta-subunit of ATP synthase can be generated and bovine F1 ATP synthase subunit can be purified as previously described (Moser et al., "Angiostatin binds ATP synthase on the surface of human endothelial cells", Proc Natl Acad Sci USA 1999;96:2811-6; Moser et al. "Endothelial cell surface F1-F0 ATP synthase is active in ATP synthesis and is inhibited by angiostatin", Proc Natl Acad Sci USA;2001; 98:6656-61). Cariporide can be solubilized in sterile water and sterile filtered.

Cell culture. A549 (human epithelial cell line derived from a lung carcinoma tissue), or an alternative cancer cell line (DU145, LNCaP, or PC-3 cells) can be obtained from, for example, the ATCC. Human umbilical vein endothelial cells (HUVEC) can be isolated from human umbilical veins as described. (Grant et al., "Matrigel induces thymosin h 4 gene in differentiating endothelial cells", J Cell Sci 1995; 108:3685-94.). HUVEC cells can be used as a positive control as a cell line that express ATP synthase on the cell surface. Cells can be cultured in DMEM (Life Technologies, Carlsbad, Calif.) with 1% penicillin streptomycin and 10% serum replacement medium 3 (Sigma, St. Louis, Mo.) to minimize the presence of plasminogen. Low-pH (6.7) medium can be prepared by reducing bicarbonate to 10 mmol/L at 5% CO2 and supplementing with 34 mmol/L NaCl to maintain osmolality or incubation of 22 mmol/L bicarbonate medium under 17% CO2 conditions. The method of lowering pH used can be varied by experimental constraints and assay.

Flow cytometry. To assure ATP synthase is functional on the cell surface of the tumor cell line, flow cytometry experiments can be performed. For example, A549 Cell lines can be cultured in varying pH medium (10, 22, and 44 mmol/L bicarbonate DMEM), under hypoxia (0.5% 02, 5% CO2, N2 balanced) versus normoxia (21% O2, 5% CO2) for 0, 12, 24, 48, and 72 hours. Live cells can be blocked, incubated with anti-β-subunit antibody, washed, blocked, incubated with a secondary goat anti-rabbit antibody-FITC (Southern Biotech, Birmingham, Ala.), and again washed, with all steps performed at 4 degrees C. Propidium iodide (BD Biosciences, San Jose, Calif.) can be included with all samples to discriminate cells with compromised membranes. The mean fluorescent intensity of FITC in 10,000 cells can be quantified by FACSCalibur flow cytometer (Becton Dickinson, Franklin Lakes, N.J.) and cells with propidium iodide uptake can be excluded to eliminate detection of mitochondrial ATP synthase on CELLQuest software (BD Biosciences).

Cell surface ATP generation assay. A549 or 1-LN cells (60,000 per well) in 96-well plates can be refreshed with medium and treated with angiostatin, angiosatain variant, anti-beta-subunit antibody, rabbit IgG raised to bovine serum albumin (Organon Teknika, West Chester, Pa.), picea-tannol (a known inhibitor of ATP synthase F1 used as a positive control, Sigma), or medium alone for 30 minutes at 37 degrees C., 5% CO2. Cells can be then incubated with 0.05 mmol/L ADP for 20 seconds. Supernatants can be removed and assayed for ATP production by CellTiterGlo luminescence assay (Promega, Madison, Wis.) as described (23). Cell lysates can be similarly analyzed to confirm that intracellular pools of ATP did not vary under any conditions. Recordings can be made on the Luminoskan Ascent (Thermo Labsystems, Helsinki, Finland). Data are expressed in moles of ATP per cell based on standards determined for each independent experiment.

Cell proliferation assay. The effect of angiostatin on cancer cell lines can be assessed with a 3-(4,5-dimethylthi-azol-2-yl)-5-(3-carboxymethoxyphenyl)- 2-(4-sulfophenyl)-2H-tetrazolium, inner salt (MTS) proliferation assay in serum-free medium. Relative cell numbers in each well of a 96-well microplate after incubation for 20 hours, 37 degrees C., and 5% $CO_2$ in the presence or absence of angiostatin can be determined using the AQueous One Cell Proliferation Assay (Promega) per protocol of the manufacturer. Medium pH can be regulated at 5% $CO_2$ through bicarbonate concentration.

Assessment of cellular cytotoxicity. To quantify cell death and cell lysis, the activity of lactate dehydrogenase (LDH) released from the cytosol into supernatant can be measured with the Cytotoxicity Detection kit (Roche, Indianapolis, Ind.). Cancer cells (e.g. A549 cells)(5,000 per well) treated with angiostatin, angiostatin variant, anti-beta-subunit antibody, rabbit IgG, cariporide, and Triton X (a detergent used to permeabilize cells as a positive control) can be incubated at 37 degrees C. and 5% $CO_2$ or 17% $CO_2$ for 15 hours at neutral and low pH conditions, respectively. An index of cytotoxicity can be calculated by dividing the average absorbance from treated samples in quadruplicate by the average absorbance from untreated samples in quadruplicate corresponding to the same pH medium. Assessment of cellular necrosis and apoptosis. To determine the mode of angiostatin induced cell death a histone-DNA ELISA can be performed. The effects of angiostatin, angiostatin variants, anti-beta-subunit antibody, rabbit IgG, and cariporide on A549 cells (5,000 per well) can be determined using an ELISA apoptosis and necrosis assay (Roche) that is dependent on detection of extranuclear histone-DNA fragments. Apoptosis or necrosis can be determined from, respectively, the cell lysates or supernatants of quadruplicate samples after 15 hours of incubation at 37 degrees C., in the presence or absence of agents. The apoptotic or necrotic indices can be calculated by dividing the average absorbance from treated samples in quadruplicate by the average absorbance from untreated samples in quadruplicate corresponding to the same pH medium. Medium pH can be regulated by incubation at 5% CO2 or 17% $CO_2$.

Intracellular pH (pHi) measurement. pHi can be measured by fluorescence in cells plated on 35-mm microwell dishes with glass coverslips (MatTek, Ashland, Mass.). Cells can be plated on growth factor-reduced, phenol-red free Matrigel (BD Biosciences). After overnight growth, medium can be changed and cells can be loaded with the pH-sensitive fluorescent dye cSNARF (Molecular Probes, Eugene, Oreg.) for 15 minutes followed by 20 minutes recovery in fresh medium. Cells can then be mounted on a microscope stage at 37 degrees C., 5% $CO_2$ for 1 hour-long collection of emission spectra from which pHi can be calculated as described from fields containing between 7 and 15 cells each (Wahl M L, Grant D S. "Effects of microenvironmental extracellular pH and extracellular matrix proteins on angiostatin's activity and on intracellular pH", Gen Pharmacol 2002;35:277-85). At the start of spectra collection, medium can be removed from the dish and cells can be challenged with 1 mL of fresh medium in the presence or absence of pH inhibitors angiostatin, anti-beta-subunit, rabbit IgG, or cariporide, a sodium-proton exchange inhibitor. Medium pH can be regulated by bicarbonate concentration, as described above, with fixed % $CO_2$.

We claim:

1. A method of preparing a conditionally active biologic protein, the method comprising steps of
   i. selecting the wild-type mammalian biologic protein;
   ii. evolving the DNA which encodes the wild-type mammalian biologic protein using one or more evolutionary techniques to create at least one mutant DNA;
   iii. expressing the at least one mutant DNA to obtain at least one mutant protein; and
   iv. modifying at least one of the peptide backbone, the amino acid side-chains and the amino or carboxyl termini of the at least one mutant protein by a chemical process or a natural process to introduce at least one modification selected from the group consisting of acetylation, acylation, PEGylation, ADP-ribosylation, amidation, covalent attachment of flavin, covalent attachment of a home moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein to obtain at least one modified mutant protein which exhibits both (a) a decrease in activity in an assay at normal physiological condition that is within a normal range of the physiological condition at a site of administration of the conditionally active protein to a subject, or at a tissue or organ at a site of action of the conditionally active protein of a subject, when compared to the activity of the wild-type protein in the assay at the same normal physiological condition, and (b) an increase in activity in an assay under aberrant condition that deviates from the normal range of the physiological condition at the site of administration of the conditionally active protein, or at the tissue or organ at the site of action of the conditionally active protein, when compared to the activity of the wild-type protein in the assay at the same aberrant condition; and
   wherein the normal physiological condition and aberrant condition are the same condition selected from the group consisting of temperature, pH, osmotic pressure, osmolality, oxidation and electrolyte concentration.

2. The method of claim 1, wherein the condition is temperature; and
   wherein the conditionally active biologic protein is inactive at the normal physiological temperature, and is active at the aberrant temperature.

3. A method of preparing a conditionally active biological response modifier, the method comprising steps of:
   a. selecting an inflammatory response mediator;
   b. identifying a wild-type antibody to the selected mediator;
   c. evolving the wild-type antibody to obtain one or more mutant antibodies;
   d. screening the one or more mutant antibodies differentially for mutants that exhibit a decreased binding affinity to the mediator in an assay at a normal physiological condition that is within a normal range of the physiological condition at a site of administration of the conditionally active protein to a subject, or at a tissue or organ at a site of action of the conditionally active protein of a subject, when compared to the binding affinity of the wild-type antibody in the assay at the same normal physiological condition, and exhibit an increased binding affinity to the mediator in an assay at an aberrant condition that deviates from the normal range of the physiological condition at the site of administration of the conditionally active protein, or at the tissue or organ at the site of action of the conditionally active protein, when compared to the binding affinity of the wild-type antibody in the assay at the same aberrant condition to identify at least one up mutant antibody; and e. modifying at least one of the peptide backbone, the amino acid side-chain and the amino or carboxyl termini of the at least one up-mutant antibody by a chemical process or a natural process introduce at least one modification selected from the group consisting of acetylation, acylation, PEGylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, proteolytic processing, phosphorylation, prenylation, racemization, selenoylation, sulfation, and transfer-RNA mediated addition of amino acids to the at least on recombined up-mutant antibody to obtain the conditionally active biological response modifier that exhibits both a decrease in binding affinity to the mediator in the assay at the same normal physiological condition, when compared to the binding affinity of the wild-type antibody in the assay at the same normal physiological condition, and an increase in binding affinity to the mediator in the assay at the same aberrant condition when compared to the binding affinity of the wild-type antibody in the assay at the same aberrant condition and wherein the normal physiological condition and aberrant condition are the same condition selected from the group consisting of temperature, pH, osmotic pressure, osmolality, oxidation and electrolyte concentration.

4. The method of claim 1, wherein the modification comprises disulfide bond formation.

5. The method of claim 1, wherein the modification comprises covalent attachment.

6. The method of claim 1, wherein the modification is selected from the group consisting of phosphorylation and acetylation.

7. The method of claim 1, wherein the evolving step comprises a process selected from the group consisting of substituting one or more nucleotides in the DNA for a different nucleotide, deleting one or more nucleotides from the DNA, and adding one or more nucleotides to the DNA.

8. The method of claim 1, wherein the evolving step comprises a technique selected from the group consisting of PCR, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis, ligase chain reaction, in vitro mutagenesis, ligase chain reaction, oligonucleotide synthesis, and combinations thereof.

9. The method of claim 1, wherein the expression step comprises expressing the mutant DNA in an expression vector selected from the group consisting of viral particles, baculovirus, phage, plasmids, phagemids, cosmids, fosmids, bacterial artificial chromosomes, viral DNA, P1-based artificial chromosomes, yeast plasmids, yeast artificial chromosomes, and combinations thereof.

10. The method of claim 9, wherein the expression vector comprises an expression control sequence to direct RNA synthesis.

11. The method of claim 1, wherein the expression step comprises expressing the mutant DNA in a host cell selected from the group consisting of bacterial cells, fungal cells, insect cells, mammalian cells, adenoviruses, and plant cells.

12. The method of claim 3, wherein the modification comprises covalent attachment.

13. The method of claim 3, wherein the modification comprises disulfide bond formation.

14. The method of claim 3, wherein the modification is selected from the group consisting of phosphorylation and acetylation.

15. The method of claim 1, wherein said at least one mutant protein obtained in step iii) is a mimetic.

16. The method of claim 1, wherein at least two said modified mutant proteins are produced by said modifying step, which at least two said modified mutant proteins exhibit both: (a) a decrease in activity in the assay at the normal physiological condition when compared to the wild-type protein at the normal physiological condition, and (b) an increase in activity in the assay at the aberrant condition when compared to the wild-type protein at the aberrant condition, and further comprising the step of selecting one said modified mutant protein which exhibits both: (a) a decrease in activity in the assay at the normal physiological condition when compared to the activity of the wild-type protein in the assay at the same normal physiological condition, and (b) an increase in activity in the assay under the aberrant condition when compared to the activity of the wild-type protein in the assay at the same aberrant condition and has a largest ratio of the activity in assay under the aberrant condition to the activity in the assay under the normal physiological condition.

17. The method of claim 1, further comprising v. repeating steps ii-iv, as necessary, to obtain at least two said conditionally active biologic proteins which exhibit both:(a) a decrease in activity in the assay at the normal physiological condition when compared to the activity of the wild-type protein in the assay at the same normal physiological condition, and (b) an increase in activity in the assay under the aberrant condition when compared to the activity of the wild-type protein in the assay at the same aberrant condition.

18. The method of claim 17, wherein the modification is selected from disulfide bond formation and covalent attachment.

19. The method of claim 17, wherein the modification is selected from the group consisting of phosphorylation and acetylation.

20. The method of claim 1, wherein the conditionally active biologic protein has a length shorter than the wild-type mammalian biologic protein.

21. The method of claim 3, wherein the conditionally active biological response modifier has a length shorter than the wild-type antibody.

22. The method of claim 17, wherein the conditionally active biologic protein has a length shorter than the wild-type mammalian biologic protein.

23. The method of claim 1, wherein the condition is pH.

24. The method of claim 1, wherein the condition is temperature.

25. The method of claim 1, wherein the condition is electrolyte concentration.

26. The method of claim 3, wherein the condition is pH.

27. The method of claim 3, wherein the condition is temperature.

28. The method of claim 3, wherein the condition is electrolyte concentration.

29. The method of claim 3, wherein at least two up-mutant antibodies are identified in step (d), further comprising the step of recombining at least one heavy chain and at least one light chain of the at least two up-mutant antibodies to create at least one recombined up-mutant antibody between steps (d) and (e) and wherein step (e) is carried out on the recombined up-mutant antibody.

30. The method of claim 1, wherein the activity is selected from the group consisting of enzyme activity, and binding activity.

31. The method of claim 30, wherein the activity is binding activity and the binding activity is binding to an antigen.

* * * * *